United States Patent
Taniguchi et al.

(10) Patent No.: US 9,198,599 B2
(45) Date of Patent: Dec. 1, 2015

(54) MAGNETIC RESONANCE IMAGING APPARATUS

(75) Inventors: Yo Taniguchi, Kokubunji (JP);
Yoshitaka Bito, Kokubunji (JP);
Tetsuhiko Takahashi, Tokyo (JP);
Takenori Murase, Kashiwa (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 562 days.

(21) Appl. No.: 13/642,573

(22) PCT Filed: Apr. 20, 2011

(86) PCT No.: PCT/JP2011/059746
§ 371 (c)(1),
(2), (4) Date: Oct. 22, 2012

(87) PCT Pub. No.: WO2011/132715
PCT Pub. Date: Oct. 27, 2011

(65) Prior Publication Data
US 2013/0049753 A1 Feb. 28, 2013

(30) Foreign Application Priority Data

Apr. 22, 2010 (JP) ................................ 2010-098591
Dec. 13, 2010 (JP) ................................ 2010-276863

(51) Int. Cl.
*A61B 5/055* (2006.01)
*G01R 33/56* (2006.01)
*G01R 33/561* (2006.01)
*A61B 5/00* (2006.01)
*G06T 5/00* (2006.01)

(52) U.S. Cl.
CPC ............... *A61B 5/055* (2013.01); *A61B 5/0042* (2013.01); *G01R 33/5608* (2013.01); *G01R 33/5613* (2013.01); *G06T 5/009* (2013.01); *A61B 2576/026* (2013.01); *G06T 2207/10088* (2013.01)

(58) Field of Classification Search
CPC ...................................................... A61B 5/055
USPC ............................................................ 324/309
See application file for complete search history.

(56) References Cited

U.S. PATENT DOCUMENTS

| | | | |
|---|---|---|---|
| 6,658,280 B1 * | 12/2003 | Haacke | 600/410 |
| 8,422,756 B2 * | 4/2013 | Haacke et al. | 382/131 |
| 2007/0238954 A1 * | 10/2007 | White et al. | 600/407 |
| 2007/0291184 A1 * | 12/2007 | Harville et al. | 348/745 |
| 2008/0071167 A1 * | 3/2008 | Ikedo et al. | 600/419 |

(Continued)

FOREIGN PATENT DOCUMENTS

| | | |
|---|---|---|
| JP | 4-364829 | 12/1992 |
| JP | 6-78900 | 3/1994 |

(Continued)

*Primary Examiner* — Rodney Fuller
(74) *Attorney, Agent, or Firm* — Baker Botts L.L.P.

(57) ABSTRACT

Image processing techniques which enable various contrast control, by quantitatively handling a degree of phase enhancement in a contrast control as a post-processing of the image reconstruction. A complex operation is performed on each pixel value of a complex image obtained by an MRI, thereby generating an image with desired contrast. Intensity is controlled by increasing or decreasing the argument of the pixel value of each pixel by a constant amount, and the degree of phase enhancement is controlled by multiplying the phase (argument) of each pixel by a constant.

19 Claims, 10 Drawing Sheets

(56) References Cited

U.S. PATENT DOCUMENTS

2009/0261824 A1* 10/2009 Haacke et al. ............... 324/307
2010/0022869 A1* 1/2010 Kimura ....................... 600/419
2010/0026299 A1* 2/2010 King et al. .................. 324/309
2014/0219533 A1* 8/2014 Sato et al. ................... 382/131

FOREIGN PATENT DOCUMENTS

| JP | 2010-46475 | 3/2010 |
| WO | WO 2010/073923 A1 | 7/2010 |

* cited by examiner 710 (w=2)

720 (w=1)

711 (w=2)

721 (w=1)

MAGNETIC RESONANCE IMAGING APPARATUS

CROSS-REFERENCE TO RELATED APPLICATIONS

This application is a national stage application under 35 U.S.C. §371 of International Application No. PCT/JP2011/059746, filed on Apr. 20, 2011, which claims priority to Japanese Application No. 2010-098591, filed on Apr. 22, 2010, and Japanese Application No. 2010-276863, filed on Dec. 13, 2010, each of which is incorporated by reference in its entirety, and from which priority is claimed.

TECHNICAL FIELD

Background Art

A magnetic resonance imaging (MRI) apparatus is a medical-use diagnostic imaging apparatus which applies a radio frequency magnetic field and a magnetic field gradient to a subject placed in a static magnetic field, measures a signal caused by nuclear magnetic resonance being generated from the subject, and creates an image. Generally, in the MRI apparatus, a slice magnetic field gradient identifying an imaging plane is applied, and simultaneously an excitation pulse (radio frequency magnetic field pulse) is provided for exciting magnetization within the plane. This allows acquisition of a nuclear magnetic resonance signal (echo) that is generated at the stage of convergence of the excited magnetization. On this occasion, in order to provide the magnetization with positional information, a phase encoding magnetic field gradient and a readout magnetic field gradient being perpendicular to each other within the imaging plane, are applied during the period from the excitation until obtaining the echo. Then, the echoes being measured are placed on the k-space where the lateral axis corresponds to kx and the longitudinal axis corresponds to ky, and an image is reconstructed by the inverse Fourier transform.

A pixel value of the reconstructed image corresponds to a complex number including magnitude (absolute value) and argument (phase). The absolute value and the argument are determined by imaging parameters such as a type of imaging sequence, a pixel size, and a repetition time; magnetization density in the subject; relaxation times (T1, T2); a spatial distribution of resonance frequencies, and the like.

In general diagnosis, a grayscale picture (absolute value image) is used, assuming the absolute value as a gray level. The absolute value image excels in visualizing a structure of a region of interest, and typically, a density weighted image, T1 and T2 weighted image, a diffusion weighted image, and an angiogram, are examples of this kind of absolute value image. On the other hand, a phase difference occurs because tissues have various resonance frequencies, respectively. Therefore, in some cases, a grayscale picture (phase image) assuming the argument (phase) as a gray level is used so as to visualize this phase difference. In particular, a high-field MRI apparatus with at least 3 T (tesla) allows visualization of fine differences in frequencies with respect to each tissue.

As thus described, it is general that either of the following information items is used for an image; the absolute value or the argument. There is also known a method which combines the absolute value and the phase to visualize brain veins with high contrast (e.g., see Patent Document 1). This method transforms the argument of each pixel into a phase image with a value range [−π, π], and further creates a phase mask with the value range being transformed to [0, 1]. Then, the phase mask is multiplied by itself q times (q≥1) and then a multiplication product of the phase mask and the absolute value of the same pixel is obtained. A value of q is determined so that CNR (contrast to noise) is maximized. According to the processes above, a difference between tissues caused by the phase difference is enhanced, and a high contrast image can be obtained.

By way of example, in a tomographic view of the brain, in general, there is a tendency that the phase of the cerebral parenchyma is positive and the phase of veins is small (negative) relative to the cerebral parenchyma. In this connection, all the positive phase is transformed to unity, and all the negative phase is transformed to [0, 1], thereby creating the phase mask. The phase mask created as described above is multiplied against the absolute value image, q number of times, thereby reducing the intensity of the veins, and then it is possible to obtain an image where the veins are enhanced.

PRIOR ART DOCUMENT

Patent Document

Patent Document 1
U.S. Pat. No. 6,658,280 Specification

DISCLOSURE OF INVENTION

Problem to be Solved by the Invention

As discussed above, the phase of each pixel of a reconstructed image is significant information which allows visualization of a difference between tissues. Therefore, as disclosed in the patent document 1, with the use of the phase information, it is possible to show a particular tissue with enhanced contrast. Here, the phase corresponds to an angle of a rotating magnetization vector, and it is susceptible not only to a difference in resonance frequencies between tissues, but also to static magnetic field strength and echo time (TE) being an imaging parameter. The method disclosed in the Patent Document 1 does not handle the phase information quantitatively, and therefore, failing to eliminate the effect of such imaging conditions. Therefore, the method of the Patent Document 1 fails to compare images subjected to the contrast control according to this method, if they are taken with various static magnetic field strengths, and/or taken with various TEs, and the phase information is not fully exploited.

The present invention has been made in view of the situation above, and an object of the present invention is to provide an image processing technique which allows utilization of the phase information quantitatively and effectively, in a contrast control as a post-processing of the image reconstruction, thereby enabling various contrast control.

Means to Solve the Problem

The present invention subjects each pixel value of a complex image obtained by MRI, to a transformation process according to a complex operation, thereby generating an image with desired contrast. This transformation includes a process to increase or decrease by a constant amount a phase (argument) of a pixel value of each pixel; and a process to multiply by a constant the phase (argument) of the pixel value of each pixel, and accordingly, implements each of the following controls quantitatively, a control of intensity and a control of phase enhancement degree (a degree of phase enhancement).

Specifically, a magnetic resonance imaging apparatus is provided, including an imaging unit for applying a radio frequency magnetic field and a magnetic field gradient to a subject placed in a static magnetic field, and detecting a nuclear magnetic resonance signal generated from the subject as a complex signal, a control unit for controlling an operation of the imaging unit, a computing unit for carrying out an operation on the complex signal and generating an image, and a display unit for displaying the image being generated, the computing unit being provided with an image reconstruction unit for reconstructing from the complex signal, a complex image having a pixel value each being a complex number, and an image transformation unit for transforming the pixel value of each pixel in the complex image according to a complex operation which carries out at least one of rotation and projection within a complex plane, so as to obtain an image with desired contrast, and generating an image where the pixel value after being transformed is set as the pixel value of each pixel.

In addition, the image transformation unit may be provided with an intensity enhancing unit for performing the transformation so that the intensity of a representative pixel being typical in a region of interest becomes a desired intensity value. Specifically, the intensity enhancing unit for projecting each of the pixel value onto a second line, passing through the origin at a predetermined first angle with respect to a first line, connecting a point of the pixel value in a region of interest on the complex plane with an origin of the complex plane.

In addition, the image transformation unit may be provided with a phase enhancing unit for performing the transformation prior to executing the intensity enhancing unit, so that a phase difference from the representative pixel is increased by a predetermined multiplication factor. Specifically, the image transformation unit may be provided with the phase enhancing unit which multiplies the argument of each pixel value on the complex plane, by a predetermined real number.

The image transformation unit may further be provided with an argument transformation unit for performing an argument transformation process which transforms the argument of each pixel value in the complex image so that the intensity in the region of interest becomes a desired intensity value, and a difference from the argument in the region of interest is increased by a predetermined multiplication factor w, and an image generation unit for setting a real part of the pixel value of each pixel after the argument transformation process, to be a new pixel value of each pixel.

In addition, there is provided an image processing method according to the computing unit in a magnetic resonance imaging apparatus including an imaging unit for applying a radio frequency magnetic field and a magnetic field gradient to a subject placed in a static magnetic field and detecting a nuclear magnetic resonance signal generated from the subject as a complex signal, a control unit for controlling an operation of the imaging unit, the computing unit for carrying out an operation on the complex signal to generate an image, and a display unit for displaying the image being generated, the image processing method being provided with an image reconstruction step of reconstructing from the complex signal, a complex image with each pixel value being a complex number, and an image transformation step of transforming the pixel value of each pixel in the complex image by a complex operation which executes at least one of rotation and projection in the complex plane so that an image with desired contrast is obtained, and generating an image setting the pixel value after being transformed as the pixel value of each pixel.

Effect of the Invention

According to the present invention, in the contrast control as a post-processing of the image reconstruction, it is possible to utilize the phase information quantitatively and effectively, accommodating various contrast control.

BEST MODE FOR CARRYING OUT THE INVENTION

Hereinafter, an explanation will be made as to an embodiment to which the present invention is applied. Hereinafter, in the entire drawings for explaining the embodiments of the present invention, a constituent having the same function is labeled the same, and tedious explanations shall not be made.

Figure 1:
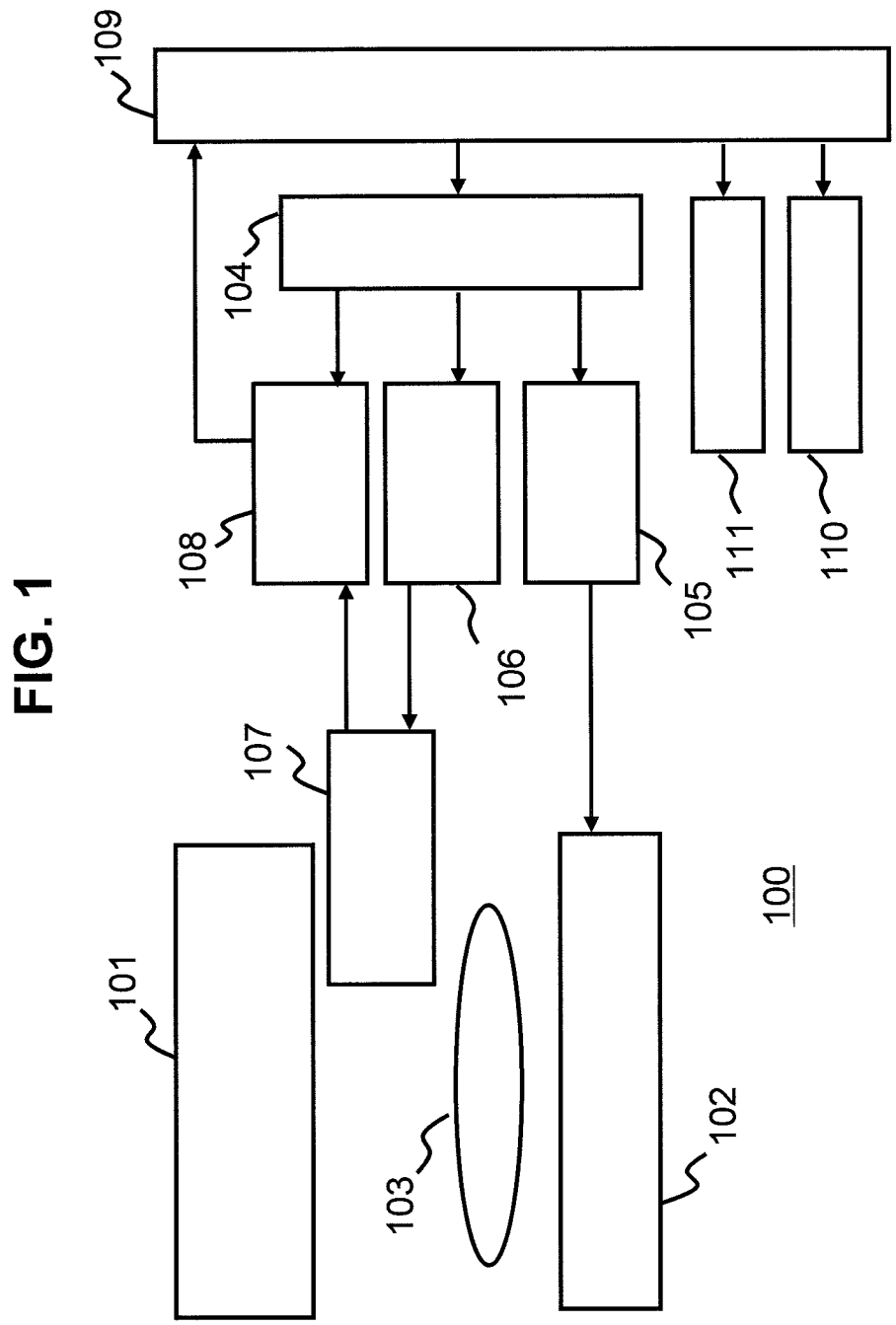
FIG. 1 is a block diagram showing a schematic configuration of an MRI apparatus according to an embodiment of the present invention.

Firstly, the MRI apparatus according to the present embodiment will be explained. FIG. 1 is a block diagram showing the schematic configuration of the MRI apparatus according to the present embodiment. The MRI apparatus 100 is provided with a magnet 101 for generating a static magnetic field, a gradient coil 102 for generating a magnetic field gradient, a sequencer 104, a magnetic field gradient power supply 105, a radio frequency magnetic field generator 106, a probe 107 for irradiating a radio frequency magnetic field and detecting a nuclear magnetic resonance signal (echo), a receiver 108, a computer 109, a display unit 110, and a storage medium 111. A subject (e.g., a living body) 103 is loaded on a bed (table) or the like, and placed within the static magnetic field space generated by the magnet 101.

The sequencer 104 sends a command to the magnetic field gradient power supply 105 and the radio frequency magnetic field generator 106, so as to generate the magnetic field gradient and the radio frequency magnetic field, respectively. The radio frequency magnetic field being generated is applied to the subject 103 via the probe 107. The probe 107 receives an echo generated from the subject 103, and the echo undergoes detection by the receiver 108. The sequencer 104 sets a nuclear magnetic resonance frequency (detection reference frequency $f_o$) as a reference of detection. Signals having undergone the detection are transferred to the computer 109, and subjected to a signal processing such as the image reconstruction. The display unit 110 displays a result of the signal processing. If needed, the storage medium 111 may store the detected signals and measurement conditions.

The sequencer 104 controls each element to operate with the timing and strength as programmed in advance. A program describes specifically about the timing and strength of the radio frequency magnetic field, magnetic field gradient, and signal receiving, is referred to as a pulse sequence. There are known various pulse sequences depending on purpose. The MRI apparatus 100 according to the present embodiment employs a GrE pulse sequence which obtains a difference in resonance frequencies between tissues as phase information. The GrE pulse sequence includes an RF-spoiled GRASS sequence, for instance.

Figure 2:
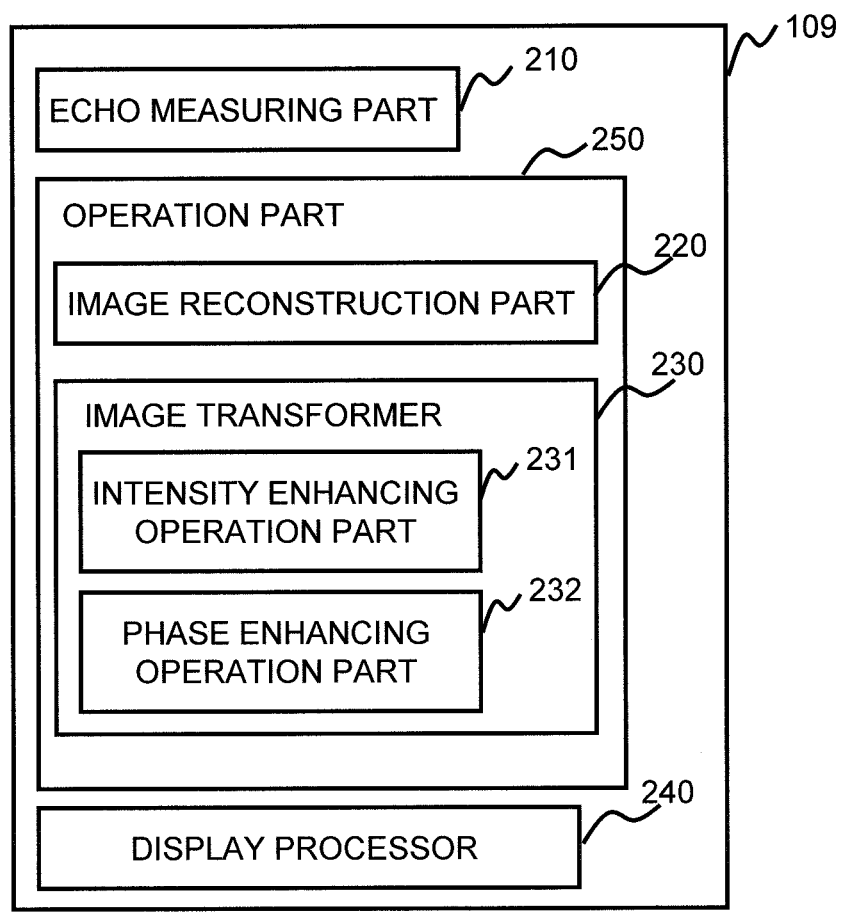
FIG. 2 is a functional block diagram of a computer according to an embodiment of the present invention.

The computer 109 of the present embodiment activates each element of the MRI apparatus 100 according to the pulse sequence, measures echoes, and obtains an image with desired contrast, from the echoes being measured. In order to implement the above procedure, as shown in FIG. 2, the computer 109 of the present embodiment is provided with an echo measuring part 210 which instructs the sequencer 104 to measure the echoes and places the echoes thus obtained on the k-space, an operation part 250 which carries out an operation on the echoes placed on the k-space to generate an image, and a display processor 240 which displays the obtained image on the display unit 110. The operation part 250 is provided with an image reconstruction part 220 for reconstructing a complex image from the echoes placed on the k-space, and an image transformer 230 for carrying out a predetermined operation on the complex image being reconstructed to generate a real number image with desired contrast.

The CPU in the computer 109 loads on its memory, the programs stored in the storage medium 111, and executes those programs, thereby implementing each of the functions in the computer 109.

Figure 3:
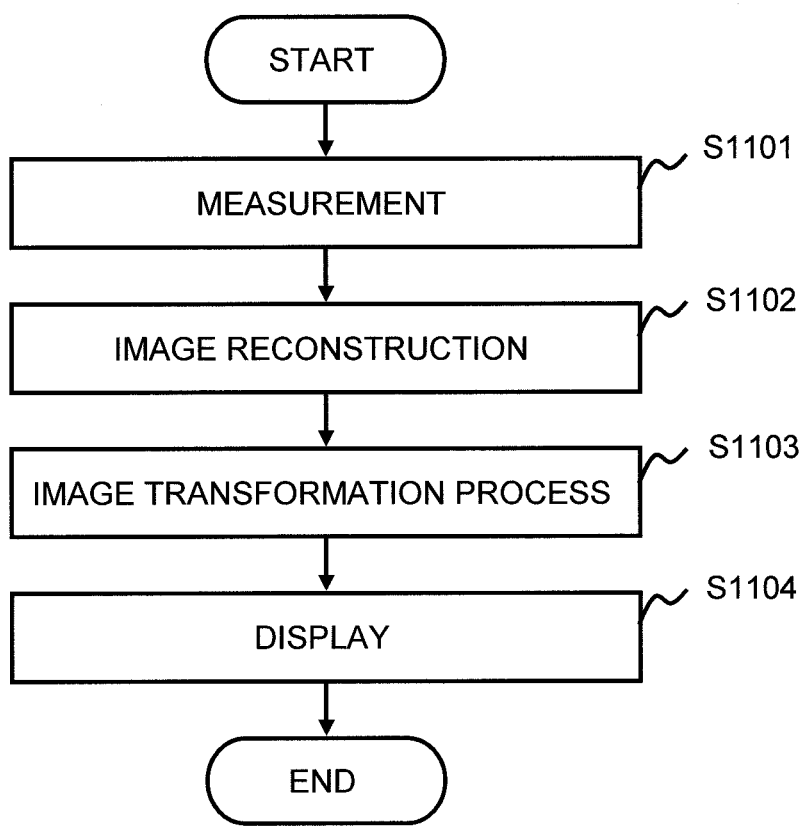
FIG. 3 is a flowchart of an imaging process according to an embodiment of the present invention.

Next, FIG. 3 shows a flow of the imaging process according to the present embodiment, being executed by the computer 109 provided with those functions above.

Upon accepting an instruction to start imaging with the setting of various imaging conditions, such as TE, the echo measuring part 210 carries out the measurement for acquiring echo signals being sufficient for enabling the reconstruction of one image, according to a predetermined pulse sequence, and placing the echo signals on the k-space (step S1101). Thereafter, the image reconstruction part 220 reconstructs an image from the echo signals placed on the k-space (image reconstruction process; step S1102). Here, a complex image is obtained. Then, the image transformer 230 subjects each pixel value of the obtained complex image to the transformation process, thereby obtaining a real number image in which each pixel value is a real number (image transformation process; step S1103). Then, the display processor 240 displays thus obtained real number image on the display unit 110, in the form of a grayscale picture (step S1104).

Next, detailed explanations will be made as to the processing performed by the echo measuring part 210, the image reconstruction part 220, and the image transformer 230.

Figure 4:
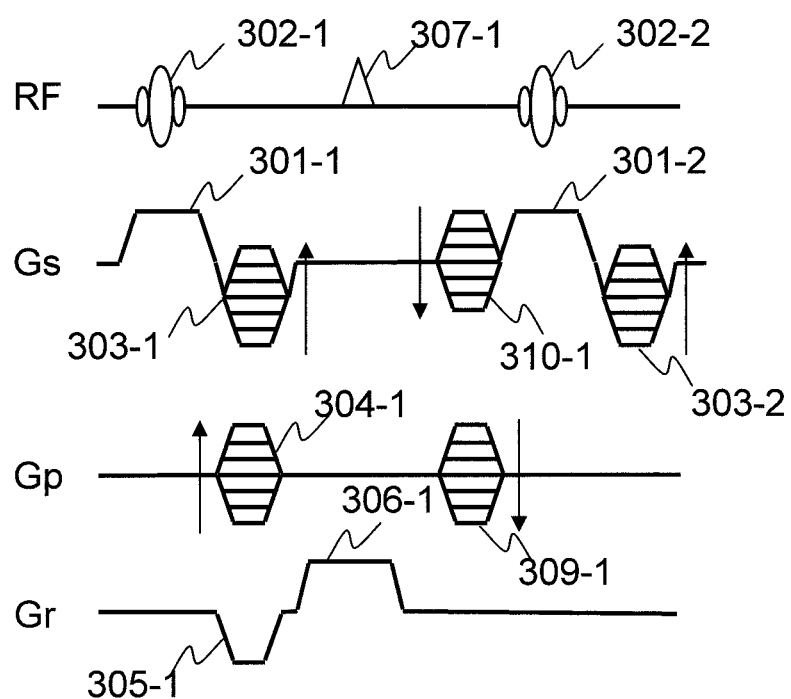
FIG. 4 is a pulse sequence diagram of an RF-spoiled GRASS sequence diagram.

The echo measuring part 210 provides an instruction to the sequencer 104 according to the predetermined pulse sequence, collects echoes, and places the echoes on the k-space. The present embodiment employs the GrE pulse sequence as described above. Here, an explanation will be made as to the RF-spoiled GRASS sequence as an example of the GrE pulse sequence that is used in the present embodiment. FIG. 4 is a diagram of the pulse sequence. In this figure, RF, Gs, Gp, and Gr represent, respectively, the radio frequency magnetic field, a slice magnetic field gradient, a phase encoding magnetic field gradient, and a readout magnetic field gradient.

In the RF-spoiled GRASS sequence, irradiation of the radio frequency magnetic field (RF) pulse 302 is performed together with applying the slice magnetic field gradient pulse 301, thereby exciting magnetization of a predetermined slice within the subject 103. Next, a slice encoding magnetic field gradient pulse 303 and a phase encoding magnetic field gradient pulse 304 are applied, so as to add positional information to the magnetization phase in the slice direction and in the phase encoding direction. After a readout magnetic field gradient 305 for dephasing is applied, one nuclear magnetic resonance signal (echo) 307 is measured, while applying the readout magnetic field gradient pulse 306 for adding positional information in the readout direction. Finally, a slice encoding magnetic field gradient pulse 310 for rephasing and a phase encoding magnetic field gradient pulse 309 are applied.

The echo measuring part 210 repeatedly executes the aforementioned procedure every repetition time TR, with varying the strength of the slice encoding magnetic field gradient pulses 303, 310 (slice encoding amount ks) and the phase encoding magnetic field gradient pulses 304 and 309 (an amount of phase encoding kp), and the phase of the RF pulse, thereby measuring echoes necessary for obtaining one image. The phase of the RF pulse is increased every time by 117 degrees, for instance. In FIG. 4, the number following the hyphen indicates the number of repeated times.

Each of the echoes being measured is placed on the three-dimensional k-space having coordinate axes, kr, kp, and ks. On this occasion, one echo occupies one line which is parallel to the kr-axis on the k-space. A absolute value image obtained by the RF-spoiled GRASS sequence becomes T1 (longitudinal relaxation time) weighted image, upon setting TE (echo time: time period from irradiation of the RF pulse 302 to the echo measurement 307) to be short, whereas upon setting the TE to be long, the absolute value image becomes T2* weighted image in which phase dispersion in the pixels is reflected.

The image reconstruction part 220 subjects the echoes (data) placed on the k-space to a process such as the three-dimensional inverse Fourier transform, and performs the image reconstruction process to reconstruct a complex image in which each pixel is represented as a complex number.

The image transformer 230 subjects each of the pixel values of the complex image reconstructed by the image reconstruction part 220 to the transformation process according to a complex operation, and performs the image transformation process for generating a real number image. The image transformation process renders a tissue to be enhanced (a tissue of interest) to have desired intensity, and simultaneously enhances the phase with a predetermined degree of enhancement.

Specifically, the image transformer 230 transforms the pixel value s of each pixel in the complex image being reconstructed, according to the formula (1), and obtains the real number image in which the pixel value of each pixel is

[Formula 1]

$$s_1 = \left| \mathrm{Re}\left[ \frac{(se^{-i\theta_1})^w}{|s|^{w-1}} e^{i\theta_0} \right] \right| \quad (1)$$

Here, i represents an imaginary unit, $\theta_1$ represents an argument of the pixel value in the tissue of interest, and w represents a multiplication factor of the argument, indicating the degree of phase enhancement. It is to be noted here that w is a real number greater than or equal to zero. The condition of w=1 keeps a phase difference between the pixels unchanged. In addition, $\theta_0$ is an angle for determining the intensity, and it determines the intensity of the tissue of interest.

A pixel corresponding to the tissue of interest is specified at an identical position on the image previously obtained, or on the absolute value image generated from the image reconstructed by the image reconstruction part according to a conventional method, and thereafter, the argument $\theta_1$ of the pixel value in the tissue of interest is determined in advance, using an argument of the specified pixel. In general, the argument of the pixel value of a vein in the image is subject to change, depending on a degree of blood oxygenation, a ratio between the blood and other tissues within a voxel, and the like. Therefore, all the values are not the same, and they have a predetermined distribution. In this connection, for example, a typical pixel (representative pixel) is determined, and the argument of its pixel value is used as the argument $\theta_1$. In order to obtain preferable contrast across the image, it is alternatively possible to configure such that an average value is used, as to the arguments of the pixel values of the respective pixels within the tissue of interest in the image.

The angle for determining intensity $\theta_0$ is expressed as $\theta_0 = \arccos(t)$, or $\theta_0 = \arcsin(t) - \pi/2$ (here, "arccos" indicates arc cosine, and "arcsin" indicates arc sine), by using an intensity coefficient t ($0 \le t \le 1$) for determining the intensity of the tissue of interest. By way of example, when the intensity coefficient t of the tissue of interest is set to be zero to render the intensity of the tissue of interest to be zero, the angle for determining intensity $\theta_0$ is set to be $\pi/2$ or $-\pi/2$. On the other hand, when the intensity coefficient t of the tissue of interest is set to be the maximum (1) and the intensity is not reduced, the angle for determining intensity $\theta_0$ is set to be zero. When the angle for determining intensity $\theta_0$ is set to be $\pi/3$ or $-\pi/3$, the intensity of the tissue of interest becomes a half of the absolute value of the original pixel value. The intensity in the area other than the tissue of interest is determined by the angle for determining intensity $\theta_0$ and the multiplication factor w.

The formula (1) expresses the transformation in which the pixel value s of each pixel is multiplied by $\exp(-i\theta_1)$, thereby decreasing the argument by $\theta_1$, setting the exponent w to multiply the argument by w, thereafter divided by $(|s|^{w-1})$ to resume the size, and multiplied by $\exp(i\theta_0)$ to increase the argument by $\theta_0$, then obtaining the absolute value of the real part. With reference to FIG. 5, the image transformation process on the complex plane according to this formula (1) will be explained.

Figure 5A:
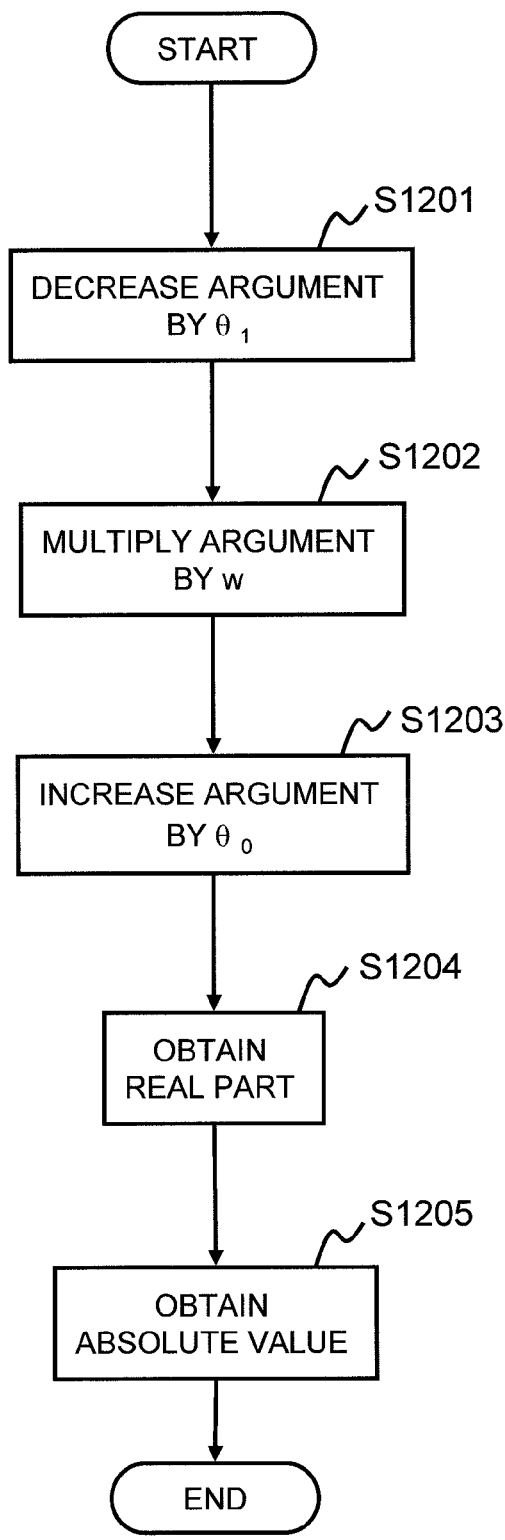
FIG. 5A is a flowchart of the image transformation process according to an embodiment of the present invention.

FIG. 5A is a processing flow for explaining the flow of the image transformation process according to the image transformer 230. FIG. 5B to FIG. 5G illustrate modes of action on the complex plane, provided to the pixel value respectively by the processes in the steps in FIG. 5A. FIG. 5B to FIG. 5G are complex planes (Gauss planes), setting the horizontal axis as a real axis (Re), and the vertical axis as an imaginary axis (Im). Here, an explanation will be made taking an example that a vein is assumed as the tissue of interest, the argument multiplication factor w is assumed as 2, and the angle for determining intensity $\theta_0$ is assumed as $\pi/2$. According to the transformation with the settings as described above, the intensity of the vein becomes lowered, and the phase contrast between tissues is doubled.

Figure 5B:
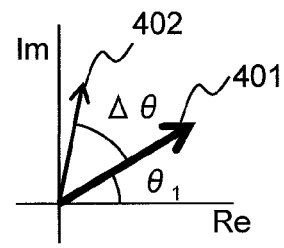
FIG. 5B illustrates influence on the complex plane, the influence exerted on the pixel value by the image transformation process according to an embodiment of the present invention.

As shown in FIG. 5B, the pixel values of the respective pixels in the complex image that is reconstructed by the image reconstruction part 220 are plotted on the complex plane. Here, the reference numeral 401 indicates the pixel value of the vein. The reference numeral 402 indicates a representative pixel value of the pixel in any other tissue. The argument of the vein pixel value 401 is assumed as $\theta_1$, and the argument of the other tissue pixel value 402 is assumed as different from the vein pixel value 401 by $\Delta\theta$.

Figure 5C:
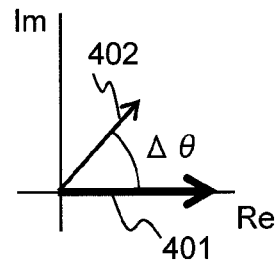
FIG. 5C illustrates influence on the complex plane, the influence exerted on the pixel value by the image transformation process according to an embodiment of the present invention.

Firstly, the arguments of the pixel values of the respective pixels are decreased by $\theta_1$ (step S1201). Here, the process for reducing the arguments of the pixel values of the respective pixels by $\theta_1$ corresponds to a process on the complex plane where the pixel values of the respective pixels are turned in clockwise about the origin only by $\theta_1$. Accordingly, as shown in FIG. 5C, the pixel value 401 of the representative pixel of the vein coincides with the real axis (Re).

Figure 5D:
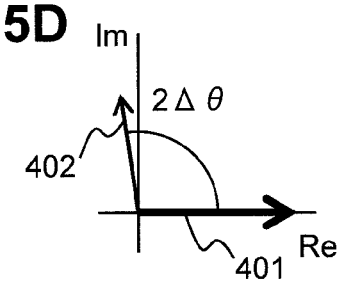
FIG. 5D illustrates influence on the complex plane, the influence exerted on the pixel value by the image transformation process according to an embodiment of the present invention.

Next, the arguments of the pixel values of the respective pixels are multiplied by w (doubled) (step S1202). At this point, the pixel value 401 does not undergo any change since it is positioned on the real axis and the argument is zero. On the other hand, the difference $\Delta\theta$ between the argument of the pixel value 402 and the argument of the pixel value 401 becomes doubled ($2\Delta\theta$). Accordingly, as shown in FIG. 5D, the difference (phase difference) between the argument of the vein and that of the tissue other than the vein is increased, being multiplied by w.

Next, the arguments of the pixel values of the respective pixels are increased by $\theta_0$ ($\pi/2$) (step S1203). This process corresponds to a process on the complex plane, where the pixel values of the respective pixels are turned in anticlockwise about the origin by $\theta_0$. According to the processing as described above, as shown in FIG. 5E, the vein pixel value 401 coincides with the imaginary axis (Im).

Figure 5E:
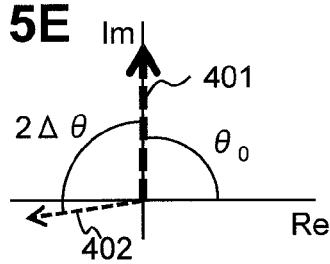
FIG. 5E illustrates influence on the complex plane, the influence exerted on the pixel value by the image transformation process according to an embodiment of the present invention.
Figure 5F:
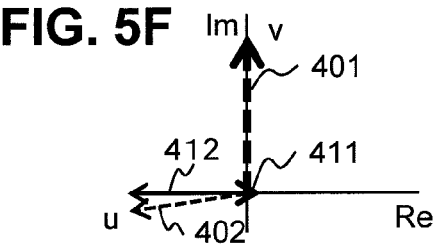
FIG. 5F illustrates influence on the complex plane, the influence exerted on the pixel value by the image transformation process according to an embodiment of the present invention.

Then, the real parts of the pixel values of the respective pixels are obtained (step S1204). As shown in FIG. 5F, here, projections (411, 412) of the respective pixel values on the real axis (Re) are obtained. According to this process, the vein pixel value 401 on the imaginary axis (Im) forms a projection image 411 whose size is zero. On the other hand, the other tissue pixel value 402 becomes the real part 412 with the doubled argument difference (phase difference) relative to the argument of the vein.

Figure 5G:
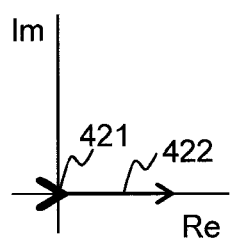
FIG. 5G illustrates influence on the complex plane, the influence exerted on the pixel value by the image transformation process according to an embodiment of the present invention.

Then, as shown in FIG. 5G, the absolute values 421 and 422 of the pixel values after the projections are taken (step S1205), respectively, assuming those absolute values as pixel values after the respective pixels are subjected to the image transformation process.

In the real image obtained according to the processing as described above, the intensity of the vein becomes zero, whereas the intensity of the other tissue becomes equal to the intensity of the image whose phase difference from the vein is doubled, relative to the phase difference of the complex image after the reconstruction. Under the condition that TE is constant, the image having a phase difference relative to the phase of vein, being twice as large as the difference of the complex image after the reconstruction, corresponds to an image that is acquired by an MRI apparatus having static magnetic field strength doubling that of the MRI apparatus which is used to obtain the original image. By way of example, in the case where the static magnetic field strength of the MRI apparatus used for acquiring the original image is 1.5 Tesla, the real image corresponds to the image that is obtained by the MRI apparatus having static magnetic field strength of 3 Tesla. On the other hand, if the static magnetic field strength is assumed as constant, this real image corresponds to an image obtained under the condition that TE is doubled.

As described above, according to the present embodiment, each pixel value of the complex image obtained by the reconstruction is subjected to the transformation according to complex operation, and it is possible to create an image with desired contrast. This transformation includes a process for increasing or decreasing the phase (argument) of the pixel value of each pixel, by a certain amount, and a process for multiplying the phase (argument) of each pixel by a constant, and accordingly implements the control of intensity and the control of the phase enhancement degree (the degree of phase enhancement), each quantitatively. As thus described, according to the present embodiment, it is possible to render a desired tissue to have desired intensity, and further, the degree of phase enhancement reflecting the influence of the static magnetic field strength and TE is quantitatively controllable. Therefore, by the use of phase information, it is possible to eliminate the impact of the difference in static magnetic field strength and TE for showing the phase contrast between tissues. According to the present embodiment, the phase information is effectively utilized, thereby enabling implementation of various contrast control, in the post-process after the image acquisition.

According to the present embodiment, since the degree of phase enhancement is handled quantitatively, it is possible to control the degree of phase enhancement depending on the imaging conditions such as the static magnetic field strength and TE which have an influence on the phase. As discussed above, the GrE pulse sequence is employed in the present embodiment. The argument of the pixel value in the image obtained by the GrE pulse sequence is approximately proportional to the static magnetic field strength and TE. Therefore, in the present embodiment, the multiplication factor w is adjusted to transform the argument of each pixel value, to the argument of the pixel value in an image taken with the static magnetic field strength and TE which are different from those when actual imaging is performed.

By way of example, when the image transformation process with the setting the multiplication factor w to 2, according to the image transformer 230 of the present embodiment, is performed to the image obtained by the MRI apparatus with the static magnetic field strength 1.5 Tesla, the phase of each tissue becomes approximately equivalent to that of the image which is taken by the apparatus with the static magnetic field strength of 3 Tesla, being doubled in strength. Therefore, it is possible to obtain from the image taken by the 1.5 Tesla MRI apparatus, phase contrast corresponding to that of the image taken by the apparatus with the static magnetic field strength of 3 Tesla.

On the other hand, according to the present embodiment, an approximately identical degree of phase enhancement can be obtained as to the images taken under the conditions where the static magnetic field strength and TE are variously changed.

By way of example, when the image A taken with the static magnetic field strength being $B_a$ (T) and TE being $TE_a$ (ms) undergoes the image transformation process of the present embodiment with the conditions that $\theta_1=\theta_{1a}$ and $w=w_a$, and the image B taken with the static magnetic field strength being $B_b$ (T) and TE being $TE_b$ (ms) undergoes the image transformation process according to the method of the present embodiment with the conditions that $\theta_1=(\theta_{1a} \times B_b \times TE_b/B_a/TE_a)$ and $w=(w_a \times B_a \times TE_a/B_b/TE_b)$, and both images show approximately the same degree of image enhancement.

In addition, according to the present embodiment, based on an image taken under a certain condition, it is possible to obtain phase enhancement of a predicted image which is taken under a different condition.

By way of example, when an image $A_e$ is generated after subjecting the image A taken with the static magnetic field strength $B_a$ (T) and TE being $TE_a$(ms) to the image transformation process under the conditions that $\theta_1=\theta_{1a}$ and $w=w_a$, and the same image A is subjected to the image transformation process of the present embodiment under the conditions that $\theta_1=f_{1a}$ and $w=(w_a \times B_p \times TE_p/B_a/TE_a)$, it is possible to predict an image $B_e$ which is obtained by taking an image of the same subject with the static magnetic field strength being $B_p$ (T) and TE being $TE_p$ (ms) and performing the same image transformation process thereon.

According to this method, it is possible to virtually generate contrast of images under various imaging conditions. By way of example, using the image taken by a 3 Tesla apparatus, it is possible to virtually create an image which is taken by a 7 Tesla apparatus having a higher magnetic field. Just multiplying w by 7/3 enables estimation of the 7 Tesla image from the 3 Tesla image.

In the present embodiment, when the image transformation process is performed with setting the multiplication factor w to 1, a tissue of interest is made to have desired intensity without the phase enhancement.

In the image transformation process performed by the image transformer 230, it is sufficient if all the transformation elements included in the aforementioned formula (1) are applied to the pixel value of each pixel of the reconstructed image, and the order of those elements does not matter.

For example, the formula (1) is modified as the following formula (2), and the processes of the aforementioned step S1201 and step S1202 are carried out in the order as the following; i.e., the argument of the pixel value s of each pixel is multiplied by w and then decreased by $(w \times \theta_1)$:

[Formula 2]

$$s_1 = \left| \text{Re} \left[ \frac{(s^w e^{-i w \theta_1})^w}{|s|^{w-1}} e^{i \theta_0} \right] \right| \quad (2)$$

Alternatively, the formula (1) may be modified as the formula (3) in the following, and it is possible to configure such that the argument of the pixel value s of each pixel is multiplied by w and each pixel is projected on the line which forms the angle for determining intensity $\theta_0$ with the pixel value of the representative pixel in the tissue of interest, and the absolute value of the pixel value is taken:

[Formula 3]

$$s_1 = \left| \text{Re} \left[ \frac{s^w e^{i(\theta_0 - w \theta_1)}}{|s|^{w-1}} \right] \right| \quad (3)$$

With reference to FIG. 6, there will be explained a flow of the image transformation process according to the image transformer 230 for the above case, and a mode of action performed on the pixel value in each step of the process. Here, similar to FIG. 5, the vein is assumed as the tissue of interest, and the multiplication factor w is set to be 2. FIG. 6A is a processing flow for explaining the flow of the image transformation process. FIG. 6B to FIG. 6F illustrate modes of action provided to the pixel value respectively by the processes in the steps in FIG. 6A, on the complex plane setting the horizontal axis as a real axis (Re), and the vertical axis as an imaginary axis (Im). Settings of other conditions are the same as those in FIG. 5.

Figure 6A:
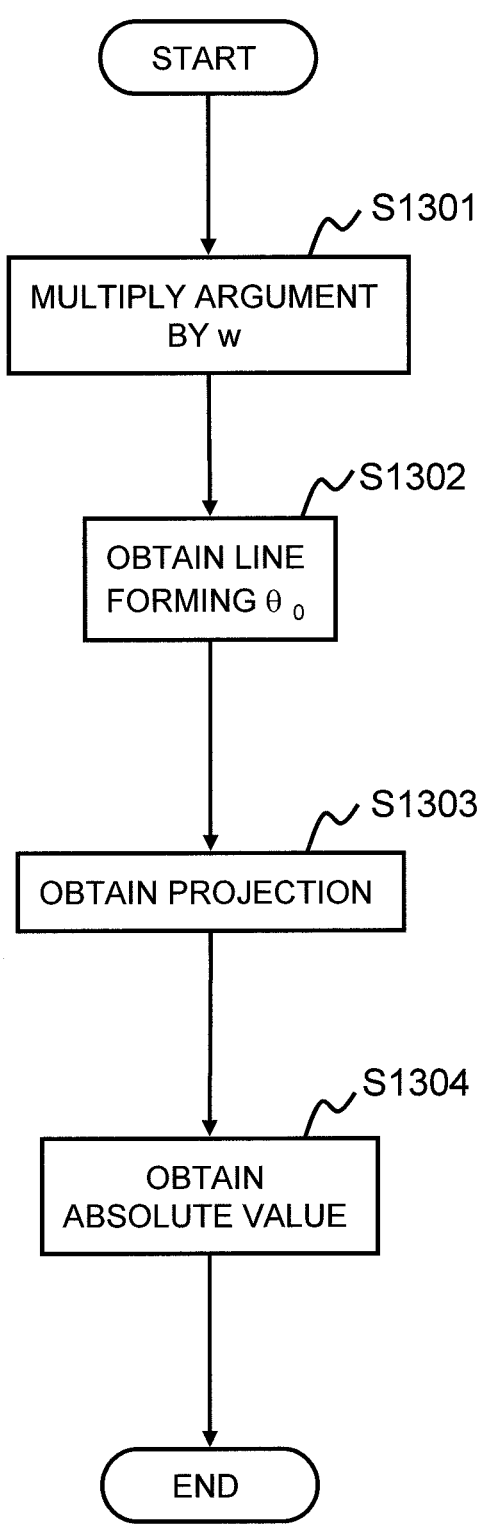
FIG. 6A is a flowchart of a modified example of the image transformation process according to an embodiment of the present invention.
Figure 6B:
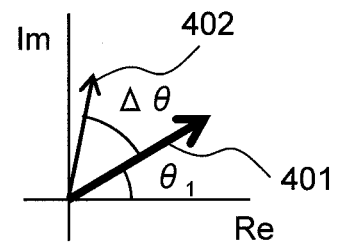
FIG. 6B illustrates influence on the complex plane, the influence exerted on the pixel value by the modified example of the image transformation process according to an embodiment of the present invention.

The pixel values of the respective pixels in the complex image that is reconstructed by the image reconstruction part 220 are plotted on the complex plane as shown in FIG. 6B.

Figure 6C:
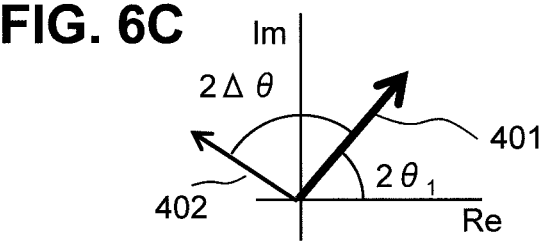
FIG. 6C illustrates influence on the complex plane, the influence exerted on the pixel value by the modified example of the image transformation process according to an embodiment of the present invention.
Figure 6D:
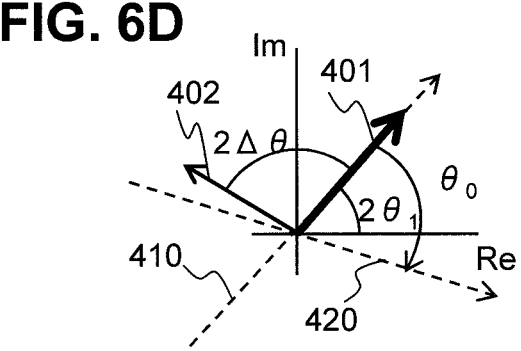
FIG. 6D illustrates influence on the complex plane, the influence exerted on the pixel value by the modified example of the image transformation process according to an embodiment of the present invention.
Figure 6E:
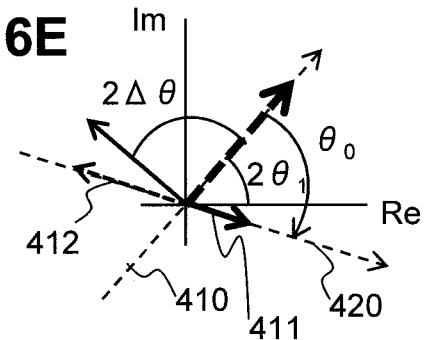
FIG. 6E illustrates influence on the complex plane, the influence exerted on the pixel value by the modified example of the image transformation process according to an embodiment of the present invention.
Figure 6F:
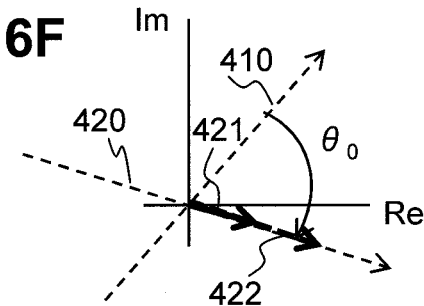
FIG. 6F illustrate influence on the complex plane, the influence exerted on the pixel value by the modified example of the image transformation process according to an embodiment of the present invention.

Firstly, as shown in FIG. 6C, the arguments of the pixel values of the respective pixels are multiplied by w (doubled) (step S1301). Then, as shown in FIG. 6D, a line (the second line) 420 is obtained, which forms the angle (the first angle) $\theta_0$ with the line (the first line) 410 made by the pixel value 401 of the representative pixel of the vein (step S1302). As shown in FIG. 6E, there are obtained projections 411 and 412 of the respective pixel values of the pixels onto the line 420 (step S1303). Then, as shown in FIG. 6F, the absolute values (421, 422) of the projections are taken (step S1304), and they are respectively set as the pixel values of the pixels after the image transformation process.

According to the processing above, the intensity of the tissue other than the vein is equivalent to that of the image in which a phase difference from the vein is doubled relative to the complex image after the reconstruction. By way of example, if the $\theta_0$ is assumed as $\pi/2$, the line 410 made by the vein pixel value 401 is orthogonal to the line 420. Therefore, its projection 411 becomes zero.

It is further possible to configure the processes from the steps S1301 to S1303 such that the arguments of the pixel values of the respective pixels are multiplied by w, then the pixel values of the respective pixels are turned about the origin by the second angle $(\theta_0 - w \theta_1)$, the line 420 is made to coincide with the real axis (Re), and projection onto the real axis is obtained (e.g., a real part is obtained).

Furthermore, the processes from the steps S1201 to S1203 in FIG. 5 may be carried out in the order that the argument $\theta_1$ of the pixel value of the representative pixel is subtracted from the argument of the initial pixel value s of each pixel, the pixel value of each pixel after the subtraction is divided by the absolute value of the initial pixel value s of each pixel, then the value being obtained is raised to the power of (w−1), the result is multiplied by the initial pixel value s, and thereafter, the argument of the pixel value of each pixel is increased by $(\theta_0 - \theta_1)$.

In the present embodiment, a predetermined one value is employed as the argument $\theta_1$ of the pixel value of the tissue of interest, but this is not the only example. It is further possible that the image transformation process is performed while changing $\theta_1$, various post-process images being displayed, and allowing an inspector to visually decide $\theta_1$ which depicts the tissue of interest the best. It should be noted that an optimum $\theta_1$ value remains almost unchanged even when the subject is different, as far as the pulse sequence, the static magnetic field strength, and the TE are the same. Therefore, once the optimum $\theta_1$ value is predetermined according to some subjects used as examples, and stores the optimum value, it is not necessary to obtain the optimum $\theta_1$ value every time an image is taken.

Here, a detailed explanation will be made as to the image transformation process according to the image transformer 230, for each pixel value of the complex image. As described above, the image transformation process includes, a process for rendering the intensity of the tissue to be enhanced (tissue of interest) to have desired intensity (intensity enhancing process), and a process for allowing the phase to be enhanced, using a predetermined degree of enhancement (phase enhancing process). In order to implement these processes, the image transformer 230 is provided with an intensity enhancing operation part 231 and a phase enhancing operation part 232.

The intensity enhancing operation part 231 carries out operation to increase or decrease the phase (argument) of the pixel value of each pixel by a certain amount, in order to set the intensity targeted for the enhancement to be the desired intensity. The operation for increasing or decreasing the phase (argument) of the pixel value of each pixel by a certain amount, corresponds to a process to rotate the complex vector on the complex plane as shown in FIG. 5B, FIG. 5C, and FIG. 5E. Therefore, the operation executed by the intensity enhancing operation part 231 is referred to as an operation of argument rotation.

The phase enhancing operation part 232 carries out the operation to raise each pixel value to the power of a real number in order to enhance the phase with a predetermined degree of enhancement. As shown in FIG. 5D, the operation for calculating each pixel value raised to the power of a real number corresponds to a process to multiply the phase (argument) of each pixel by a constant. Therefore, the operation executed by the phase enhancing operation part 232 is referred to as an operation of argument real-number multiplication.

In other words, each of the aforementioned formulas (1), (2), and (3) includes the operation of argument rotation and the operation of argument real-number multiplication. As described above, for example, the formula (1) includes the operation of argument rotation for decreasing the argument by $\theta_1$ by multiplying the pixel value s of each pixel by $\exp(-i\theta_1)$, the operation of argument real-number multiplication for multiplying the argument by w, using the power of w, then dividing the result by ($|s|^{w-1}$) obtained by calculating the absolute value of the pixel value s raised to the power of (w−1), thereby resuming the size, and the operation of argument rotation for multiplying the argument by $\exp(i\theta_0)$ to increase the argument by $\theta_0$.

In a general computer, it is difficult to directly handle a complex number, and therefore, when the computer 109 actually executes the operation of argument rotation and the operation of argument real-number multiplication as described above, a transformation is performed to establish an operation which uses a real part and an imaginary part of a complex value. One example of this transformation will be explained.

Firstly, the operation of argument rotation according to the intensity enhancing operation part 231 will be explained in detail. This operation is executed in the aforementioned steps S1201 and S1203 of the image transformation process as shown in FIG. 5A. The intensity enhancing operation part 231 of the present embodiment uses the real part and the imaginary part of the complex number, so as to perform the operation of argument rotation which rotates the argument of the complex number by a given angle $\theta$.

In general, if the real part and the imaginary part of the complex number z are assumed as a and b, respectively, the complex number z is expressed by the following formula (4) in the orthogonal form:

$$z = a + ib \tag{4}$$

Here, i is an imaginary unit ($i^2 = -1$).

The operation for rotating the argument of the complex number z by a given angle $\theta$ corresponds to the process for rotating the complex vectors (a, b) by $\theta$ on the complex space. When the complex number after the transformation is assumed as $z_1$ ($z_1 = a_1 + ib_1$), the complex vectors ($a_1$, $b_1$) after the transformation are expressed by the following formula (5), using a rotation matrix:

[Formula 5]

$$\begin{pmatrix} A \\ B \end{pmatrix} = \begin{pmatrix} \cos\theta & -\sin\theta \\ \sin\theta & \cos\theta \end{pmatrix} \begin{pmatrix} a \\ b \end{pmatrix} \tag{5}$$

When this is expanded, the complex number $z_1$ after the transformation is expressed by the formula (6):

[Formula 6]

$$z_1 = a\cos[\theta] - b\sin[\theta] + i(b\cos[\theta] + a\sin[\theta]) \tag{6}$$

The intensity enhancing operation part 231 of the present embodiment uses the aforementioned formula (6) to rotate the complex vector of the pixel value s, and obtains a pixel value after the rotation.

Next, a detailed explanation will be made as to the operation of argument real-number multiplication according to the phase enhancing operation part 232. This operation corresponds to the operation used in the step S1202 shown in the aforementioned FIG. 5A. The phase enhancing operation part 232 of the present embodiment performs a binomial expansion of the complex number in the orthogonal form, thereby calculating the complex number raised to the power of a real number.

If the real part and the imaginary part of the complex number z are assumed as a and b, respectively, the complex number z is expressed by the aforementioned formula (4) in the orthogonal form. Before using the binomial expansion, the formula (4) is firstly modified as the following formula (7):

$$z = a(1 + ib/a) \tag{7}$$

On this occasion, the complex number z raised to the power of w is expressed by the following formula (8):

$$z^w = a^w(1 + ib/a)^w \tag{8}$$

The binomial expansion is performed through conditional branching based on the size correlation between the real part a and the imaginary part b.

When $|a| \geq |b|$, if it is assumed that $x = b/a$, the aforementioned formula (8) is expressed by the following formula (9):

$$z^w = a^w(1 + ix)^w \tag{9}$$

Here, when $(1+ix)^w$ ($|ix|<1$) is expanded according to the binomial expansion, $z^w$ is expressed by the following formula (10):

[Formula 10]

$$z^w = a^w(1+ix)^w = \sum_{k=0}^{\infty} \binom{w}{k}(ix)^k \tag{10}$$

Here, $$\binom{w}{k} = \frac{(w)_k}{(k)_k}$$

$$(w)_k = w(w-1)(w-2)\ldots(w-k+1)$$

On the other hand, when $|a|<|b|$, it is assumed that $x = a/b$ in the aforementioned formula (8), and if further modified, it is expressed as the following formula (11):

[Formula 11]

$$z^w = a^w(1+ix)^w = i^w b^w(1-ix)^w \tag{11}$$

Here, when $(1-ix)^w$ ($|-ix|<1$) is expanded according to the binomial expansion, $z^w$ is expressed by the following formula (12):

[Formula 12]

$$z^w = i^w b^w(1-ix)^w = \sum_{k=0}^{\infty} \binom{w}{k}(-ix)^k \tag{12}$$

Here, $$\binom{w}{k} = \frac{(w)_k}{(k)_k}$$

$$(w)_k = w(w-1)(w-2)\ldots(w-k+1)$$

The phase enhancing operation part 232 of the present embodiment expands the aforementioned formula (10) and the formula (12) using a predetermined order, and performs the operation of argument real-number multiplication. Hereinafter, specific expansion examples of the aforementioned formula (10) and the formula (12) will be shown, taking an example that they are expanded to the fifth order.

When the formula (10) under the condition that $|a| \geq |b|$ is expanded to the fifth order, it is expressed as the following formula (13):

[Formula 13]

$$z^w = (1/120)a^w(120+120iwx-60(-1+w)wx^2-20i(-2+w)(-1+w)wx^3+5(-3+w)(-2+w)(-1+w)wx^4+i(-4+w)(-3+w)(-2+w)(-1+w)wx^5) \quad (13)$$

When $a<0$, if w is not integer, $a^w$ becomes a complex number, and therefore for carrying out the operation of the formula (13), further conditional branching is performed based on the plus or minus sign of a, as the following.

When $a \geq 0$, x is returned to b/a and the real part and the imaginary part are respectively integrated in the formula (13), and this is expressed as the following formula (14):

[Formula 14]

$$z^w = a^w(1+(b^2w)/(2a^2)-(b^4w)/(4a^4)-(b^2w^2)/(2a^2)+(11b^4w^2)/(24a^4)-(b^4w^3)/(4a^4)+(b^4w^4)/(24a^4)+i((bw)/a-(b^3w)/(3a^3)+(b^5w)/(5a^5)+(b^3w^2)/(2a^3)-(5b^5w^2)/(12a^5)-(b^3w^3)/(6a^3)+(7b^5w^3)/(24a^5)-(b^5w^4)/(12a^5)+(b^5w^5)/(120a^5))) \quad (14)$$

When $a<0$, $a^w$ is changed depending on the plus or minus sign of b. In other words, $$a^w = (-ae^{i\pi})^w \ (b \geq 0) \quad (15)$$

$$a^w = (-ae^{-i\pi})^w \ (b < 0) \quad (16)$$

When those formulas (15) and (16) are modified by the use of Euler's formula, they are expressed as the following formulas (17) and (18), respectively:

[Formula 17]

$$a^w = (-a)^w \text{Cos}[\pi w] + i(-a)^w \text{Sin}[\pi w] \ (b \geq 0) \quad (17)$$

[Formula 18]

$$a^w = (-a)^w \text{Cos}[\pi w] - i(-a)^w \text{Sin}[\pi w] \ (b < 0) \quad (18)$$

The formula (14) is modified by using the formula (17) and formula (18), and the real part and the imaginary part are respectively integrated, they are expressed as the following formulas (19) and (20) depending on the plus or minus sign of b.

[Formula 19]

$$z^w = (1/(120a^5))(-a)^w(5a(24a^4-12a^2b^2(-1+w)w+b^4(-3+w)(-2+w)(-1+w)w)\text{Cos}[\pi w]-b(120a^4-20a^2b^2(-2+w)(-1+w)+b^4(-4+w)(-3+w)(-2+w)(-1+w))w \text{Sin}[\pi w])+i(1/(120a^5))(-a)^w(b(120a^4-20a^2b^2(-2+w)(-1+w)+b^4(-4+w)(-3+w)(-2+w)(-1+w))w \text{Cos}[\pi w]+5a(24a^4-12a^2b^2(-1+w)w+b^4(-3+w)(-2+w)(-1+w)w)\text{Sin}[\pi w]) \ (b \geq 0) \quad (19)$$

[Formula 20]

$$z^w = (1/(120a^5))(-a)^w(5a(24a^4-12a^2b^2(-1+w)w+b^4(-3+w)(-2+w)(-1+w)w)\text{Cos}[\pi w]+b(120a^4-20a^2b^2(-2+w)(-1+w)+b^4(-4+w)(-3+w)(-2+w)(-1+w))w \text{Sin}[\pi w])+i(1/(120a^5))(-a)^w(b(120a^4-20a^2b^2(-2+w)(-1+w)+b^4(-4+w)(-3+w)(-2+w)(-1+w))w \text{Cos}[\pi w]-5a(24a^4-12a^2b^2(-1+w)w+b^4(-3+w)(-2+w)(-1+w)w)\text{Sin}[\pi w]) \ (b<0) \quad (20)$$

On the other hand, when the formula (12) after the binomial expansion under the condition that $|a|<|b|$ is expanded to the fifth order, for instance, $z^w$ is expressed by the following formula (21):

[Formula 21]

$$z^w = (1/120)i^w b^w(120-120iwx-60(-1+w)wx^2+20i(-2+w)(-1+w)wx^3+5(-3+w)(-2+w)(-1+w)wx^4-i(-4+w)(-3+w)(-2+w)(-1+w)wx^5) \quad (21)$$

When x is returned to a/b, the aforementioned formula (21) is expressed by the following formula (22):

[Formula 22]

$$a^w = (1/120)i^w b^w(120-(120iaw)/b-(60a^2(-1+w)w)/b^2+(20ia^3(-2+w)(-1+w)w)/b^3+(5a^4(-3+w)(-2+w)(-1+w)w)/b^4-(ia^5(-4+w)(-3+w)(-2+w)(-1+w)w)/b^5) \quad (22)$$

Here, the term $(i^w b^w)$ is changed depending on the plus or minus sign of b. In other words, $$(ib)^w = (be^{i\pi/2})^w \ (b \geq 0) \quad (23)$$

$$(ib)^w = (-be^{-i\pi/2})^w \ (b<0) \quad (24)$$

When those formulas (23) and (24) are modified by the use of Euler's formula, they are expressed as the following formulas (25) and (26), respectively:

[Formula 25]

$$(ib)^w = b^w \text{Cos}[(\pi w)/2] + ib^w \text{Sin}[(\pi w)/2] \ (b \geq 0) \quad (25)$$

[Formula 26]

$$(ib)^w = (-b)^w \text{Cos}[\pi/2] - i(-b)^w \text{Sin}[\pi/2] \ (b<0) \quad (26)$$

The formula (22) is modified by using the formula (25) and the formula (26), and the real part and the imaginary part are respectively integrated, they are expressed as the following formulas (27) and (28).

[Formula 27]

$$z^w = (1/120)b^{(-5+w)}(5b(24b^4-12a^2b^2(-1+w)w+a^4(-3+w)(-2+w)(-1+w)w)\text{Cos}[\pi w/2]+a(120b^4-20a^2b^2(-2+w)(-1+w)+a^4(-4+w)(-3+w)(-2+w)(-1+w))w \text{Sin}[\pi w/2])+(1/120)ib^{(-5+w)}(-a(120b^4-20a^2b^2(-2+w)(-1+w)+a^4(-4+w)(-3+w)(-2+w)(-1+w))w \text{Cos}[\pi w/2]+5b(24b^4-12a^2b^2(-1+w)w+a^4(-3+w)(-2+w)(-1+w)w)\text{Sin}[\pi w/2]) \ (b \leq 0) \quad (27)$$

[Formula 28]

$$z^w = (1/(120b^5))(-b)^w(5b(24b^4-12a^2b^2(-1+w)w+a^4(-3+w)(-2+w)(-1+w)w)\text{Cos}[\pi/2]-a(120b^4-20a^2b^2(-2+w)(-1+w)+a^4(-4+w)(-3+w)(-2+w)(-1+w))w \text{Sin}[\pi/2])+(1/120)i(-b)^{(-5+w)}(a(120b^4-20a^2b^2(-2+w)(-1+w)+a^4(-4+w)(-3+w)(-2+w)(-1+w))w \text{Cos}[\pi/2]+5b(24b^4-12a^2b^2(-1+w)w+a^4(-3+w)(-2+w)(-1+w)w)\text{Sin}[\pi/2]) \ (b<0) \quad (28)$$

The phase enhancing operation part 232 of the present embodiment performs the operation of argument real-number multiplication, according to any of the aforementioned formulas (14), (19), (20), (27), and (28) depending on the size correlation between a and b, and the signs thereof, within the complex number (z=a+ib) targeted for the transformation.

Next, a specific explanation will be made as to an arithmetic processing using each of the aforementioned formulas in each of the steps in FIG. 5A, in the case where the pixel value s (s=A+iB) represented as the complex number A+iB is provided.

Firstly, in the step S1201, the process is performed for reducing the argument of the pixel value s by $\theta_1$. In other words, the intensity enhancing operation part 231 carries out this calculation by using the formula (6), and obtains the calculation result $s_2$ that is expressed by the following formula (29):

[Formula 29]

$$s_2 = A \cos[-\theta_1] - B \sin[-\theta_1] + i(B \cos[-\theta_1] + A \sin[-\theta_1]) \quad (29)$$

Here, the calculation result $s_2$ is expressed by the following formula (30):

$$s_2 = A_2 + iB_2 \quad (30)$$

Next, with respect to thus obtained $s_2$, the argument is multiplied by w in the S1202. This calculation is performed by using any of the aforementioned formulas (14), (19), (20), (27), and (28) depending on the size and the sign of $A_2$ and $B_2$. On this occasion, the $A_2$ substitutes for a, and $B_2$ substitutes for b, in each of the formulas. Here, its calculation result $s_3$ is expressed by the following formula (31):

$$s_3 = A_3 + iB_3 \quad (31)$$

Next, the argument of $s_3$ is increased by $\theta_0$ in the step S1203. The intensity enhancing operation part 231 performs this calculation by using the formula (6), and obtains the calculation result $s_4$ that is expressed by the following formula (32):

[Formula 32]

$$s_4 = A_3 \cos[\theta_0] - B_3 \sin[\theta_0] + i(B_3 \cos[\theta_0] + A_3 \sin[\theta_0]) \quad (32)$$

Here, the calculation result $s_4$ is expressed by the following formula (33):

$$s_4 = A_4 + iB_4 \quad (33)$$

Then, the absolute value $|Re(s_4)|$ of the real part of $s_4$ is calculated in the steps S1204 and S1205, and the pixel value $s_1$ after the image transformation process is obtained. Here, $s_1$ is expressed by the following formula (34):

[Formula 34]

$$s_1 = |Re(s_4)| = |A_4| = |A_3 \cos[\theta_0] - B_3 \sin[\theta_0]| \quad (34)$$

So far, there has been explained a method for carrying out the calculations of the formulas (1), (2), and (3) in the present embodiment, by using the rotation matrix and the binomial expansion on the complex plane.

The explanation has been made, taking an example that the binomial expansion is performed to the fifth order, as a specific expansion example. However, the number of the order is not limited to this example. In order to obtain sufficient calculation precision, it is desirable that the order is at least the third, and equal to or larger than w.

The order applied to the binomial expansion has an impact on the precision of $s^w$ and its calculation load. In other words, when the order is made larger, a degree of precision becomes higher, whereas increasing the number of terms in the polynomial expression after the expansion may result in that the calculation load is increased. On the other hand, if the order is made smaller, the calculation time is reduced, but the precision level is lowered. It is to be noted that if the order is less than the third, or less than w, it is still possible to obtain a result, even though the precision is deteriorated.

In view of those outcomes above, an appropriate order is selected according to the multiplication factor w. By way of example, the order corresponding to the multiplication factor w is suitable from the view point of the precision and calculation time. In other words, when the maximum value of w is around five, the order is set to be the fifth.

By using the method as described above, it is possible for the image transformer 230 of the present embodiment to perform the image transformation process on each pixel value of the complex image, according to the polynomial operation using the real part value and the imaginary part value of the pixel value being the complex number. Since the polynominal operation is relatively a simple expression, implementation thereof is easy for the computer 109, and further the operation load is low, enabling a processing within a short time.

Figure 7A:
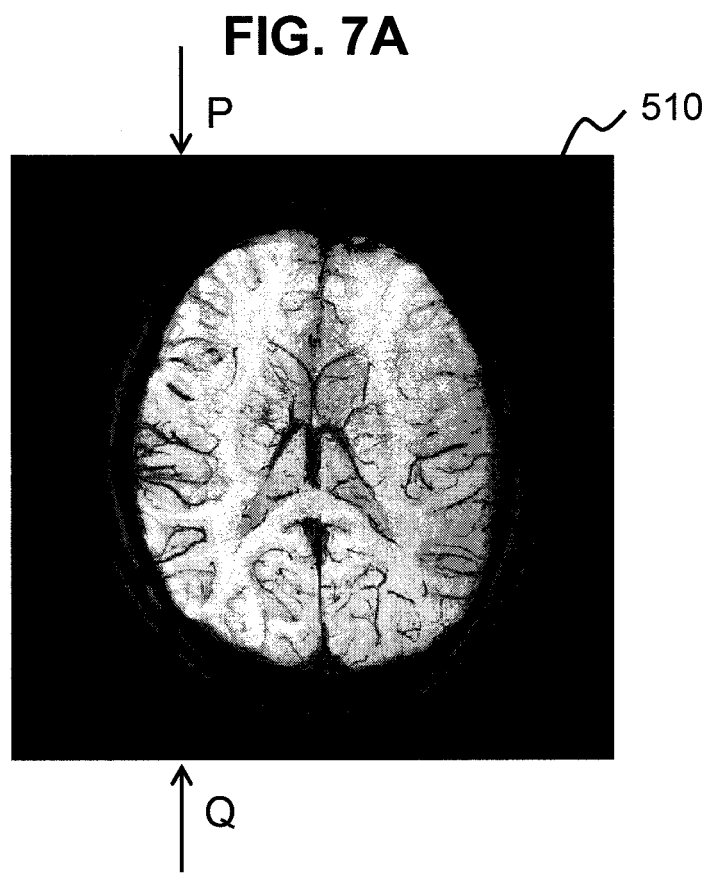
FIG. 7A illustrates one example of an image obtained after subjected to the image transformation process according to an embodiment of the present invention.
Figure 7B:
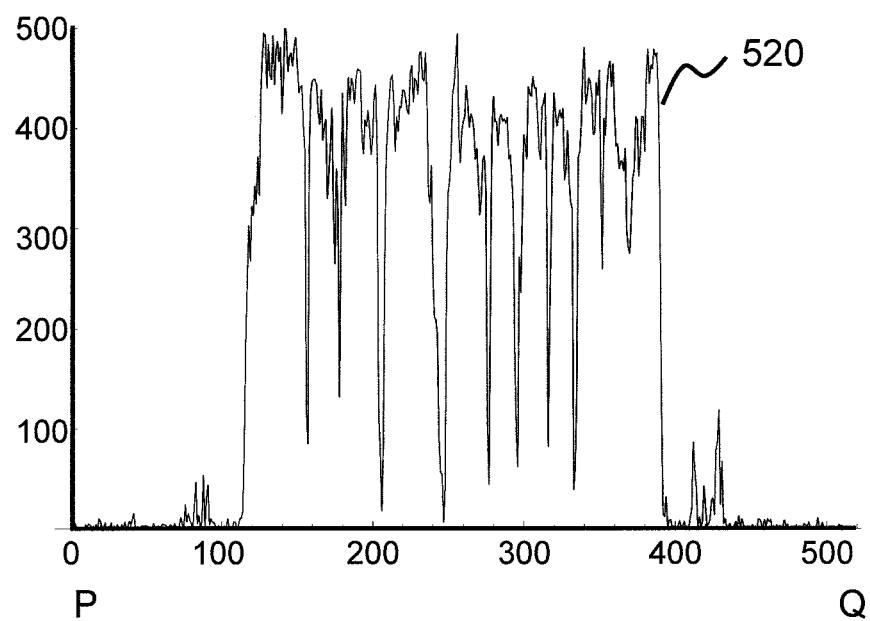
FIG. 7B illustrates an intensity profile of the image shown in FIG. 7A.

Hereinafter, an example of the image transformation process according to the present embodiment will be described. FIG. 7A and FIG. 7B show a result of the processing in the case where $\theta_1$ was determined visually, and the image transformation process of the present embodiment was performed with the setting of w=2. FIG. 7A shows an image 510 after the image transformation process of the present embodiment, and FIG. 7B shows an intensity profile 520 of the image 510, taken along the line connecting P and Q. The image 510 was obtained as a result of the image transformation process and the minimum intensity projection thereof which were performed on 10 sheets out of 80 sheets of complex images, the images being taken under the conditions that the field of view was 220×220, the matrix size was 512×512, the number of slices was 80, the slice thickness was 80 mm (one slice was 1 mm in thickness), and TR/TE was 65/40 ms. On this occasion, the optimum $\theta_1$ was −0.6 radian.

As shown in FIG. 7A, according to the image transformation process of the present embodiment, it is found that the image was visualized with preferable contrast, where the brain veins were enhanced. In addition, according to the intensity profile 520 as shown in FIG. 7B, it is found that the intensity of very fine regions corresponding to the veins was lowered and the intensity was sufficiently close to zero.

Figure 8A:
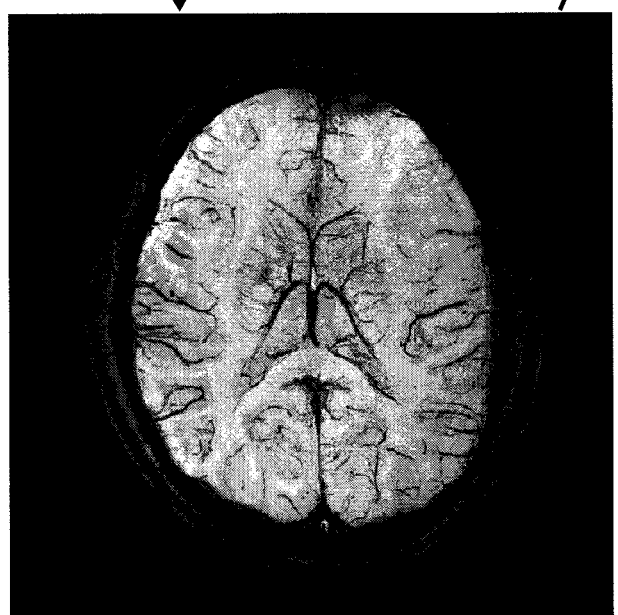
FIG. 8A illustrates one example of an image obtained after subjected to the image transformation process according to an embodiment of the present invention.
Figure 8B:
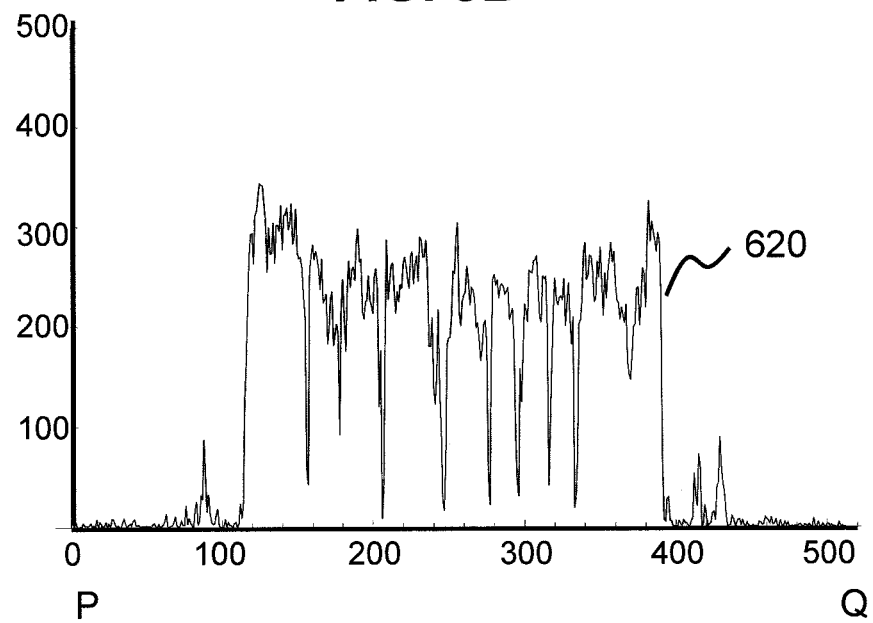
FIG. 8B illustrates an intensity profile of the image shown in FIG. 8A.

In order to verify the effect by the change of the multiplication factor w, the image transformation process of the present embodiment was performed under the condition that w=1, with the other conditions being the same as the aforementioned case as shown in FIG. 7A and FIG. 7B, and its result is shown in FIG. 8A and FIG. 8B. FIG. 8A shows an image 610 after the image transformation process, and FIG. 8B shows the intensity profile 620 along the line connecting P and Q on the image 610.

According to the intensity profile 620 of FIG. 8B, it is found that the intensity of the veins was sufficiently close to zero. However, it is also found that the region corresponding to the veins became thinner than the intensity profile 520 of FIG. 7B. Also in the image 610 of FIG. 8A, it is found that the veins were visualized finer than the image 510 of FIG. 7A. According to those results above, it is found that the degree of phase enhancement is changed depending on the multiplication factor w.

Next, by using a brain image taken by the MRI apparatus with the static magnetic field strength of 1.5 Tesla, there will be shown an example for displaying an image in which the cerebral parenchyma (white matter and gray matter) is enhanced. It is known that there is a frequency difference of approximately 6 ppm between the white matter and the gray matter. A phase difference caused by this frequency difference is enhanced and visualized as an image, thereby depicting the white matter and the gray matter with high contrast. In order to achieve this, in the example here, a setting was made as $\theta_0 = -\pi/3$ so that the intensity coefficient of the pixel having the argument between the white matter and the gray matter became ½. This was determined in this manner, so that even when the multiplication factor w was changed, strength relationship as to the intensity between the white matter and the gray matter was not changed. In addition, $\theta_1$ was determined as 0.1 visually. The multiplication factor w was set to be 1 and 2, in order to evaluate the phase corresponding to an image taken by the MRI apparatus with the static magnetic field strength of 3 Tesla, being doubled in strength. The processing target image being used was the same as that of FIG. 7A and FIG. 7B, and one sheet of the image out of 80 sheets was processed.

Figure 9A:
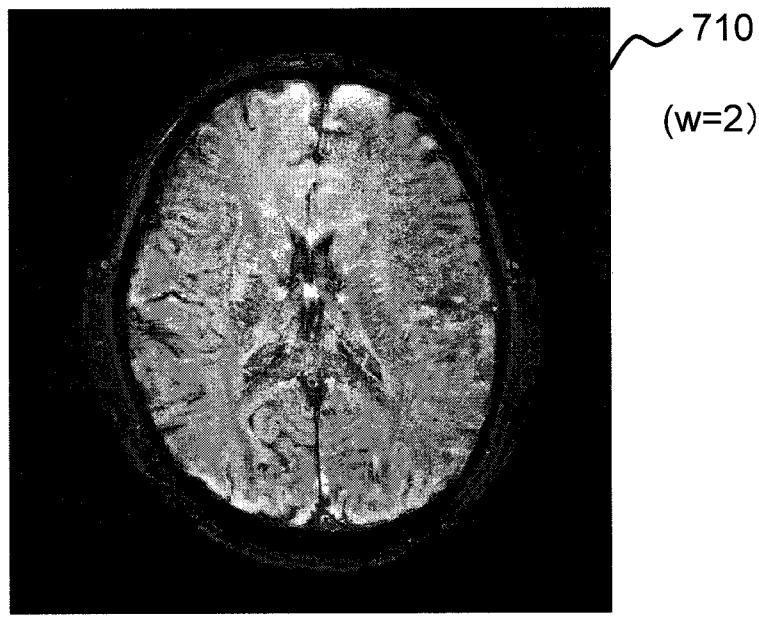
FIG. 9A illustrates examples of the image obtained after subjected to the image transformation process according to an embodiment of the present invention.
Figure 9B:
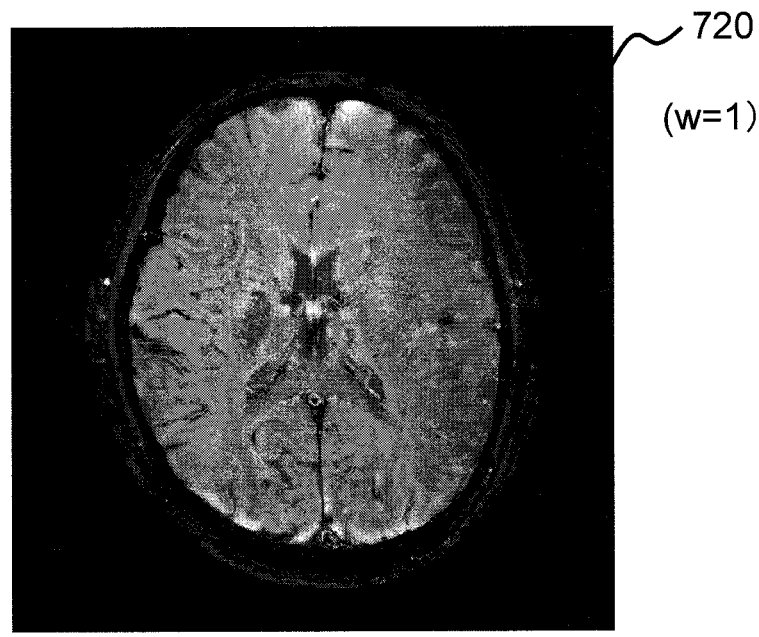
FIG. 9B illustrates examples of the image obtained after subjected to the image transformation process according to an embodiment of the present invention.

FIG. 9A shows an image 710 after the image transformation process of the present embodiment, setting the multiplication factor w to 2, and FIG. 9B shows an image 720 after the image transformation process of the present embodiment, setting the multiplication factor w to 1. As seen from FIG. 9A and FIG. 9B, according to the image transformation process of the present embodiment, the white matter and the gray matter were visualized with high contrast, and the image corresponding to 3 Tesla with the enlarged multiplication factor w shows higher contrast. In other words, it is verified that according to the image transformation process of the present embodiment, it was possible to display an image with the phase being enhanced, and virtually create image contrast under various imaging conditions.

In the embodiment as described above, the image transformer 230 obtains the real part of the pixel value after the intensity enhancing process and the phase enhancing process, and finally takes the absolute value thereof. Here, in the image transformation process of the present embodiment, a process made up of the intensity enhancing process and the phase enhancing process is referred to as an argument transformation process which transforms the argument of the pixel value s of each pixel in such a manner that the intensity of the region of interest becomes a desired intensity value, and a difference between the arguments of the pixel value s and that of the region of interest is changed with a predetermined multiplication factor. A process for obtaining the real part of the pixel value is referred to as a real number transformation process, and a process for obtaining the absolute value thereof is referred to as an absolute value process.

In other words, in the aforementioned embodiment, the image transformer 230 performs as the image transformation process; the argument transformation process, the real number transformation process, and finally performs the absolute value process. On the other hand, it is alternatively possible to skip this final absolute value process and display the real part as a gray-scale picture, without change. Also in this case, an image where the phase is enhanced can be obtained in the similar manner.

Figure 10A:
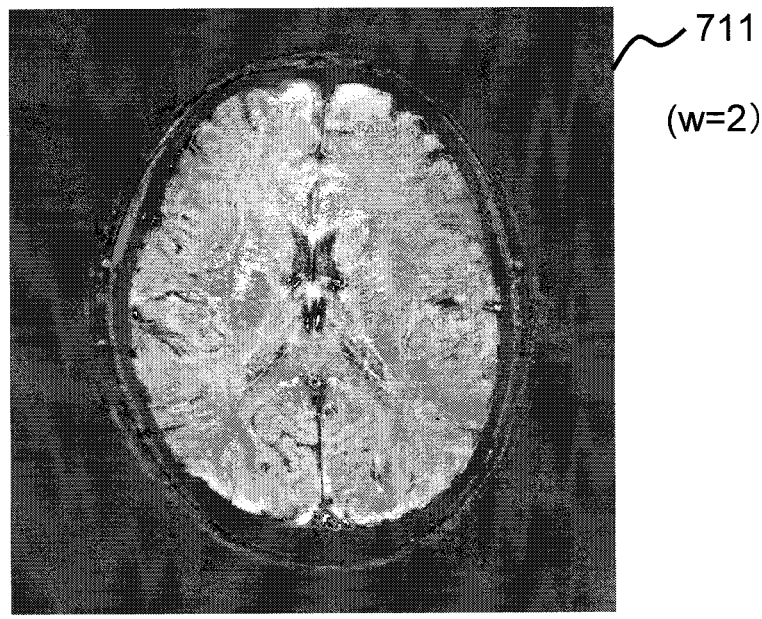
FIG. 10A illustrates examples of the image obtained after subjected to an alternative example of the image transformation process according to an embodiment of the present invention.
Figure 10B:
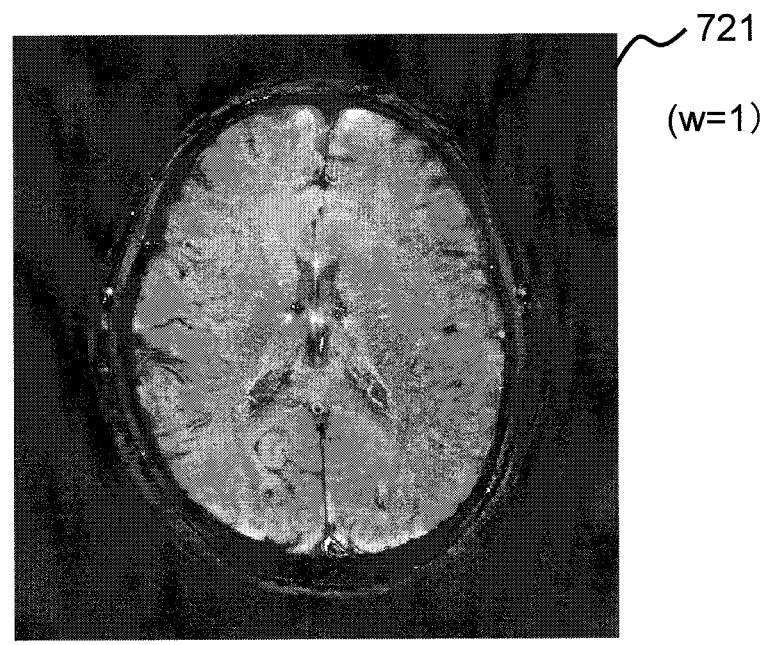
FIG. 10B illustrates examples of the image obtained after subjected to an alternative example of the image transformation process according to an embodiment of the present invention.

As a way of example, FIG. 10A and FIG. 10B show results obtained by the image transformation process in which the absolute value process was skipped. In this example here, the conditions were the same as those in FIGS. 9A and (b), but the absolute value process was skipped. FIGS. 10A and (b) show the images 711 and 721 after the image transformation process of the present embodiment, setting the multiplication factor w to 2 and 1, respectively.

The pixel value $s_5$ in this case is expressed by the following formula (35):

$$s_5 = Re[s_o] \tag{35}$$

Here, $s_0$ is a pixel value of the complex number obtained by the argument transformation process, and it is expressed by the following formula (36):

[Formula 36]

$$s_0(s) = \frac{(se^{-i\theta_1})^w}{|s|^{w-1}} e^{i\theta_0} \tag{36}$$

When the images 711 and 721 shown in FIG. 10A and FIG. 10B are respectively compared to the images 710 and 720 shown in FIG. 9A and FIG. 9B, it is found that the white matter and the gray matter were successfully visualized with high contrast in the similar manner, even though the absolute value process was not performed. As for the images 710 and 720 on which the absolute value process was performed, the intensity of the background was close to zero (black) similar to a typical MRI apparatus, whereas as for the images 711 and 712 without the absolute value process, the intensity of the background indicated intermediate density. Therefore, there is a visual difference that the background looks a little brighter.

Even when the absolute value process is skipped, it is possible to modify the real number transformation process performed on the pixel value $s_0$ after the aforementioned process as the following formula (37), in order to control the intensity of the background. The pixel value obtained on this occasion is assumed as $s_6$:

$$s_6 = Re[s_0] + |s| \tag{37}$$

Here, the absolute value of the pixel value s of each pixel is added to the pixel value $s_0$ after the argument transformation process. Accordingly, the intensity of the background with a small absolute value is kept to be small, and the intensity value covering from the negative value to a positive value (from $-|s|$ to $|s|$) is transformed to the range from the zero to positive value (from 0 to $2|s|$), thereby controlling the background to remain dark.

The imaginary part may be used instead of the real part of the pixel value $s_0$ after the argument transformation process, as the following formula (38). The pixel value obtained on this occasion is assumed as $s_7$. According to this procedure, a similar effect may be obtained as the effect of the formula (37).

$$s_7 = Im[s_0 + i|s|] \tag{38}$$

The real number transformation process is not limited to the example above, but various modifications may be possible.

When the image transformation process is carried out according to the formula (35) and the formula (37), since the absolute value process is not performed, the range of the intensity coefficient t is set to be in the range of $-1 \leq t \leq 1$. Therefore, when the intensity of the tissue of interest is minimized, the angle for determining intensity $\theta_0$ (=arccos(t)) is set to be arccos($-1$)=$\pi$, by using the minimum value ($-1$) of t.

When the image transformation process is carried out according to the formula (38), the intensity coefficient t falls in the range of $-1 \leq t \leq 1$ in the same manner. Therefore, similar to the example above, the minimum value ($-1$) is used as the value of t, to calculate the angle for determining intensity $\theta_0$, for the case where the intensity of the tissue of interest is to be minimized. On this occasion, since the projection is made on the imaginary axis, it is defined as the following: the angle for determining intensity $\theta_0$=arccos($-1$)+$\pi/2$=$3\pi/2$. It is to be noted that if the intensity of the tissue of interest is not intended to be lowered, it is defined as the following: the angle for determining intensity $\theta_0 = \arccos(1) + \pi/2 = \pi/2$.

Further in the image transformation process of the present invention, a representative pixel is determined and the argument of the pixel value is used as the argument of the tissue of interest. Actually, the arguments of all the pixel values in the tissue to be enhanced (tissue of interest) are not the same value, and have a certain distribution. For example, when the tissue of interest corresponds to a vein, as shown in FIG. 7A and FIG. 7B, an image in which the intensity of the vein being enhanced (darkened) was obtained by setting $\theta_1$ to −0.6. On the other hand, as for a thick vein or a lesion area such as bleeding, the argument of the pixel value may be smaller than −0.6 in some cases. On this occasion, if the pixel value for this case is transformed according to any of the formulas (1) to (3), the real part of the pixel whose argument is smaller than $\theta_1$ becomes a negative value, and by taking the absolute value of this value, resulting in having a positive value. In other words, the thick vein or the lesion area are displayed brightly.

In order to prevent this occurrence, the pixel having the argument smaller than $\theta_1$ is controlled to have zero intensity after the image transformation process, whereas as for the pixel having the argument larger than $\theta_1$, it is controlled so that the intensity after the image transformation process does not change.

On this occasion, each pixel value $s_1$ after the image transformation process is performed according to the following formula (39), and thus obtained pixel value $s_8$ is assumed as a final result. It is to be noted here that $s_0$ represents a pixel value after the intensity enhancing process and the phase enhancing process expressed by the formula (36) are performed.

[Formula 39]

$$s_1 = \begin{cases} s_0(|s|\exp(i\theta_{min})) & \begin{pmatrix} \theta_{min} \leq 0 \text{ and } \text{Im}(s) < 0 \text{ and} \\ \text{Im}(s \exp(-i\theta_{min})) < 0 \end{pmatrix} \text{ or} \\ & \begin{pmatrix} \theta_{min} > 0 \text{ and} \\ (\text{Im}(s) < 0 \text{ or } \text{Im}(s \exp(-i\theta_{min})) < 0) \end{pmatrix} \\ s_0(|s|\exp(i\theta_{max})) & \begin{pmatrix} \theta_{max} \geq 0 \text{ and } \text{Im}(s) > 0 \text{ and} \\ \text{Im}(s \exp(-i\theta_{max})) > 0 \end{pmatrix} \text{ or} \\ & \begin{pmatrix} \theta_{max} < 0 \text{ and} \\ (\text{Im}(s) > 0 \text{ or } \text{Im}(s \exp(-i\theta_{max})) > 0) \end{pmatrix} \\ s_1 & \text{else} \end{cases} \quad (39)$$

The image transformation according to the formula (39) allows the intensity of the pixel having the argument before the image transformation smaller than $\theta_{min}$, to have a degree of enhancement equivalent to the pixel having the argument $\theta_{min}$, and allows the intensity of the pixel having the argument before the image transformation larger than $\theta_{max}$, to have a degree of enhancement equivalent to the pixel having the argument $\theta_{max}$.

Any values are available to be set as $\theta_{min}$ and $\theta_{max}$. By way of example, if they are set as the following formulas (40) and (41), the intensity of the pixel having the argument smaller than $\theta_{min}$ becomes the minimum intensity, whereas the intensity of the pixel having the argument larger than $\theta_{max}$ does not fall to a lower level:

$$\theta_{max} = \theta_1 + |\theta_0|/w \quad (40)$$

$$\theta_{min} = \theta_{max} - \pi/2/w \quad (41)$$

The processing according to the aforementioned formula (39) is applicable not only to the $s_1$ as described above, but also to $s_5$, $s_6$, and $s_7$, being obtained by the aforementioned formulas (35), (37), and (38), respectively.

For $s_5$ obtained by the formula (35) and for $s_6$ obtained by the formula (37), $\theta'_{min}$ obtained by the following formula (42) may be used as $\theta_{min}$, instead of using the formula (41):

$$\theta'_{min} = \theta_{max} - \pi/w \quad (42)$$

With this setting above, the degree of enhancement monotonically decreases down to $\theta'_{min}$, being smaller than $\theta_{min}$.

Further, for $s_7$ obtained by the formula (38), $\theta'_{max}$ obtained by the following formula (43) may be used as $\theta_{max}$:

$$\theta'_{max} = \theta_1 + |\theta_0|/w + \pi/2/w \quad (43)$$

With this setting above, the degree of enhancement monotonically increases up to $\theta'_{max}$, being larger than $\theta_{max}$.

It is to be noted that only the image transformer 230, or both the image reconstruction part 220 and the image transformer 230 may be configured on an information processor being provided separately from the MRI apparatus 100.

Explanation of References

100: MRI apparatus, 101: magnet, 102: gradient coil, 103: subject, 104: sequencer, 105: magnetic field gradient power supply, 106: radio frequency magnetic field generator, 107: probe, 108: receiver, 109: computer, 110: display unit, 111: storage medium, 210: echo measuring part, 220: image reconstruction part, 230: image transformer, 231: intensity enhancing operation part, 232: phase enhancing operation part, 240: display processor, 250: operation part, 301: slice magnetic field gradient pulse, 302: RF pulse, 303: slice encoding magnetic field gradient pulse, 304: phase encoding magnetic field gradient pulse, 305: readout magnetic field gradient, 306: readout magnetic field gradient pulse, 307: echo, 309: phase encoding magnetic field gradient pulse, 310: slice encoding magnetic field gradient pulse, 401: vein, 402: other tissue, 411: absolute value of real part of vein, 412: absolute value of real part of other tissue, 510: image, 520: intensity profile, 610: image, 620: intensity profile, 710: image, 711: image, 720: image, 721: image

What is claimed is:

1. A magnetic resonance imaging apparatus comprising,
   an imaging unit for applying a radio frequency magnetic field and a magnetic field gradient to a subject placed in a static magnetic field, and detecting a nuclear magnetic resonance signal generated from the subject as a complex signal,
   a computing unit for carrying out an operation on the complex signal and generating an image, and
   a display unit for displaying the image being generated, the computing unit comprising,
   an image reconstruction unit for reconstructing from the complex signal, a complex image having a pixel value each being a complex number, and
   an image transformation unit for transforming the pixel value of each pixel in the complex image according to a complex operation which carries out at least one of rotation and projection within a complex plane, so as to obtain an image with desired contrast, and generating an image where the pixel value after being transformed is set as the pixel value of each pixel, wherein
   the image transformation unit comprises an intensity enhancing unit configured to project each of the pixel value onto a second line, passing through the origin at a predetermined first angle with respect to a first line, connecting a point of the pixel value in a region of interest on the complex plane with an origin of the complex plane.

2. The magnetic resonance imaging apparatus according to claim 1, wherein,
the image transformation unit comprises a phase enhancing unit for multiplying an argument of the pixel value of each pixel on the complex plane, by a predetermined real number, prior to executing the intensity enhancing unit.

3. The magnetic resonance imaging apparatus according to claim 2, wherein,
the phase enhancing unit represents the pixel value as a real part and an imaginary part, and calculates the pixel value of each pixel to be raised to the power of a real number by using a binomial expansion, thereby multiplying the argument of the pixel value by the real number.

4. The magnetic resonance imaging apparatus according to claim 3, wherein, the order of the binomial expansion is set to be not less than the fifth.

5. The magnetic resonance imaging apparatus according to claim 1, wherein,
the first angle is obtained from either arc-cosine or arc-sine of an intensity coefficient which renders the intensity of the region of interest to be a desired intensity value.

6. The magnetic resonance imaging apparatus according to claim 1, wherein,
the first angle $\theta_0$ is set to be zero, and
the region of interest is an area maximizing the intensity.

7. The magnetic resonance imaging apparatus according to claim 1, wherein,
the first angle $\theta_0$ is set to be either $\pi/2$ or $\pi$,
the region of interest is an area rendering the intensity to be zero.

8. The magnetic resonance imaging apparatus according to claim 1, wherein,
the first angle $\theta_0$ is set to be any of $-\pi/3$, $\pi/3$, $-\pi/2$, and $\pi/2$, and
the region of interest is an area rendering the intensity to be intermediate.

9. A magnetic resonance imaging apparatus comprising,
an imaging unit for applying a radio frequency magnetic field and a magnetic field gradient to a subject placed in a static magnetic field, and detecting a nuclear magnetic resonance signal generated from the subject as a complex signal,
a computing unit for carrying out an operation on the complex signal and generating an image, and
a display unit for displaying the image being generated, the computing unit comprising,
an image reconstruction unit for reconstructing from the complex signal, a complex image having a pixel value each being a complex number, and
an image transformation unit for transforming the pixel value of each pixel in the complex image according to a complex operation which carries out at least one of rotation and projection within a complex plane, so as to obtain an image with desired contrast, and generating an image where the pixel value after being transformed is set as the pixel value of each pixel, wherein
the image transformation unit comprises an intensity enhancing unit for configured to calculate, on the complex plane, a second angle being a difference between an argument of the pixel value in the region of interest and a predetermined first angle, allowing the pixel value of each pixel on the complex plane to rotate about the origin at an angle corresponding to the second angle, so that the pixel value in the region of interest forms the first angle with either the real axis or the imaginary axis on the complex plane, and calculating elements in the direction of the axis with which the pixel value in the region of interest forms a first angle, as to all the pixel values after the rotation.

10. The magnetic resonance imaging apparatus according to claim 9, wherein,
the intensity enhancing unit subjects a complex vector of the pixel value to the rotation on the complex plane by using a rotation matrix, thereby obtaining a pixel value after the rotation.

11. A magnetic resonance imaging apparatus comprising,
an imaging unit for applying a radio frequency magnetic field and a magnetic field gradient to a subject placed in a static magnetic field, and detecting a nuclear magnetic resonance signal generated from the subject as a complex signal,
a computing unit for carrying out an operation on the complex signal and generating an image, and
a display unit for displaying the image being generated, the computing unit comprising,
an image reconstruction unit for reconstructing from the complex signal, a complex image having a pixel value each being a complex number, and
an image transformation unit for transforming the pixel value of each pixel in the complex image according to a complex operation which carries out at least one of rotation and projection within a complex plane, so as to obtain an image with desired contrast, and generating an image where the pixel value after being transformed is set as the pixel value of each pixel, wherein,
the image transformation unit comprises,
an argument transformation unit configured to perform an argument transformation process for transforming an argument of the pixel value of each pixel in the complex image in such a manner that intensity of the region of interest becomes a desired intensity value, and changes a difference between the argument of the pixel value of each pixel in the complex image and the argument of the region of interest, with a predetermined multiplication factor w, and
an image generation unit for rendering either a real part or an imaginary part of the pixel value of each pixel after the argument transformation process to be a new pixel value.

12. The magnetic resonance imaging apparatus according to claim 11, wherein,
the argument transformation process assumes the argument of the pixel value in the region of interest as $\theta_1$, changes the argument of each pixel value s by the angle equivalent to $-\theta_1$, multiplies by w the argument of the pixel value of each pixel after the change, and thereafter allows the argument to change by the angle equivalent to a predetermined first angle $\theta_0$.

13. The magnetic resonance imaging apparatus according to claim 12, wherein,
the argument transformation unit allows the argument of the pixel value to change, by rotating a complex vector of the pixel value using a rotation matrix, by the angle corresponding to the change, represents the pixel value as a real part and an imaginary part, and calculates the pixel value to be raised to the power of w by using a binomial expansion, thereby multiplying the argument of the pixel value by w.

14. The magnetic resonance imaging apparatus according to claim 11, wherein,
the argument transformation process assumes the argument of the pixel value in the region of interest as $\theta_1$, changes the argument of each pixel value s by the angle equivalent to $-\theta_1$, divides the pixel value of each pixel after the change by the absolute value of the pixel value s, a resultant value being raised to the power of $(w-1)$, then multiplies a further result thereof by the pixel value s, and thereafter changes the argument of the pixel value of each pixel, by the angle equivalent to $(\theta_0-\theta_i)$ being a difference between a predetermined first angle $\theta_0$ and the argument $\theta_1$.

15. The magnetic resonance imaging apparatus according to claim 14, wherein,
the argument transformation unit allows the argument of the pixel value to change, by rotating a complex vector of the pixel value using a rotation matrix, by the angle corresponding to the change, represents the pixel value as a real part and an imaginary part, and calculates the pixel value to be raised to the power of $(w-1)$ by using a binomial expansion.

16. The magnetic resonance imaging apparatus according to claim 11, wherein,
the argument $\theta_1$ and the multiplication factor w are configured in such a manner that an equivalent degree of enhancement of the argument is obtained in the images taken under the conditions where static magnetic field strength and an echo time are variously changed, using a ratio of the static magnetic field strength and a ratio of the echo time being a time period from when the imaging unit applies the radio frequency magnetic field until acquiring the nuclear magnetic resonance signal.

17. The magnetic resonance imaging apparatus according to claim 16, wherein,
when the argument transformation process with the setting of the argument $\theta_1$ as $\theta_{1a}$ and the multiplication factor w as $w_a$ is performed on a complex image A having a combination of the static magnetic field strength and the echo time being $(B_a, TE_a)$, $\theta_1$ is set as $(\theta_{1a} \times B_b \times TE_b/B_a/TE_a)$ and w is set as $(w_a \times B_a \times TE_a/B_b/TE_b)$ for a complex image B having a combination of the static magnetic field strength and the echo time being $(B_b, TE_b)$.

18. The magnetic resonance imaging apparatus according to claim 11, wherein,
the image transformation unit configures a setting of the argument $\theta_1$ and the multiplication factor w, by using a ratio of the static magnetic field strength and a ratio of the echo time being a time period from when the imaging unit applies the radio frequency magnetic field until acquiring the nuclear magnetic resonance signal, and virtually generates contrast of an image taken under the condition where the static magnetic field strength and the echo time are different.

19. The magnetic resonance imaging apparatus according to claim 18, wherein,
when the image transformation unit performs the argument transformation process on a complex image A having a combination of the static magnetic field strength and the echo time being $(B_a, TE_a)$, with the setting of the multiplication factor w as $w_a$, the argument transformation process is performed with the setting that $w=w_a \times (B_p \times TE_E)/(B_a \times TE_a)$, thereby generating an image having the combination of the static magnetic field strength and the echo time being $(B_p \times TE_p)$.

* * * * *